US012570987B2

(12) United States Patent
Mirzadeh et al.

(10) Patent No.: US 12,570,987 B2
(45) Date of Patent: Mar. 10, 2026

(54) SYNTHETICALLY EVOLVED DNA CONSTRUCTS FOR REGULATING SIGNAL PEPTIDE PERFORMANCE AS WELL AS VECTORS, HOST CELLS AND RECOMBINANT PROTEINS THEREOF

(71) Applicant: CLONEOPT AB, Upplands Väsby (SE)

(72) Inventors: Kiavash Mirzadeh, Solna (SE); Daniel Daley, Upplands Vasby (SE); Patrick Shilling, Lynbrook (AU)

(73) Assignee: CLONEOPT AB, Upplands Väsby (SE)

( * ) Notice: Subject to any disclaimer, the term of this patent is extended or adjusted under 35 U.S.C. 154(b) by 689 days.

(21) Appl. No.: 17/797,560

(22) PCT Filed: Feb. 5, 2021

(86) PCT No.: PCT/SE2021/050083
§ 371 (c)(1),
(2) Date: Aug. 4, 2022

(87) PCT Pub. No.: WO2021/158163
PCT Pub. Date: Aug. 12, 2021

(65) Prior Publication Data
US 2024/0301432 A1     Sep. 12, 2024

(30) Foreign Application Priority Data

Feb. 7, 2020    (SE) ..................................... 2030038-0
Feb. 7, 2020    (SE) ..................................... 2030039-8
Feb. 7, 2020    (SE) ..................................... 2030040-6

(51) Int. Cl.
*C12N 15/67*        (2006.01)
*C12N 15/62*        (2006.01)
(Continued)

(52) U.S. Cl.
CPC ........... *C12N 15/625* (2013.01); *C12N 15/67* (2013.01); *C12N 15/70* (2013.01); *C12P 21/02* (2013.01); *C07K 2319/02* (2013.01)

(58) Field of Classification Search
None
See application file for complete search history.

(56) References Cited

U.S. PATENT DOCUMENTS 8,361,744 B2      1/2013   Marrichi et al.

FOREIGN PATENT DOCUMENTS

| CN | 109825488 A | 5/2019 |
| WO | 2015139046 A1 | 9/2015 |
| WO | 2016099388 A1 | 6/2016 |

OTHER PUBLICATIONS

International Search Report dated Feb. 23, 2021 issued in PCT/SE2021/050083.
(Continued)

*Primary Examiner* — Evelyn Y Pyla
*Assistant Examiner* — Jagamya Vijayaraghavan
(74) *Attorney, Agent, or Firm* — Scully, Scott, Murphy & Presser, P.C.

(57)     ABSTRACT

The present invention provides a simple and inexpensive system for regulating signal peptide performance by using a synthetically evolved nucleotide sequence. The invention further relates to an expression vector comprising the nucleotide sequence. Additionally, the present invention relates to host cell comprising the expression vector. Furthermore, the present invention relates to a recombinant protein expressed by the host cell as well as a method for expressing the recombinant protein.

14 Claims, 5 Drawing Sheets

Specification includes a Sequence Listing.

(51) Int. Cl.
    _C12N 15/70_        (2006.01)
    _C12P 21/02_        (2006.01)

(56)                    References Cited

OTHER PUBLICATIONS

Swedish Search Report dated Sep. 4, 2020 issued in 2030038-0.
Mirzadeh, K., et al. "Enhanced Protein Production in _Escherichia coli_ by Optimization of Cloning Scars at the Vector-Coding Sequence Junction", ACS Synth Biol (2015), vol. 4, No. 9, pp. 959-965.
Zhou, Y., et al., "Enhancing full-length antibody production by signal peptide engineering", Microb Cell Fact (2016), vol. 15, No. 47, pp. 1-11.
Liu, Zhi-guo, et al., "Effect of silent mutations in Translational Initial Region on the production of recombinant cutinase in _Escherichia coli_", Curr Microbial (2011), vol. 62, No. 4, pp. 1302-1307.
Simmons, L.C., et al., "Translational level is a critical factor for the secretion of heterologous proteins in _Escherichia coli_", Nat Biotechnol (1996), vol. 14, No. 5, pp. 629-634.

SEQUENCE LISTING

<160> NUMBER OF SEQ ID NOS: 62

<210> SEQ ID NO 1
<211> LENGTH: 15
<212> TYPE: DNA
<213> ORGANISM: Artificial Sequence
<220> FEATURE:
<223> OTHER INFORMATION: MalE - syn_evolved - Randomized region - short
      sequence - A14

<400> SEQUENCE: 1

-continued

```
cgtattatga aaatt                                                 15

<210> SEQ ID NO 2
<211> LENGTH: 16
<212> TYPE: DNA
<213> ORGANISM: Artificial Sequence
<220> FEATURE:
<223> OTHER INFORMATION: MalE - syn_evolved - Randomized region - short
      sequence - A2

<400> SEQUENCE: 2
tcatggaatg aagatc                                                16

<210> SEQ ID NO 3
<211> LENGTH: 16
<212> TYPE: DNA
<213> ORGANISM: Artificial Sequence
<220> FEATURE:
<223> OTHER INFORMATION: MalE - syn_evolved - Randomized region - short
      short sequence - A6

<400> SEQUENCE: 3
ttagtggatg aaaata                                                16

<210> SEQ ID NO 4
<211> LENGTH: 15
<212> TYPE: DNA
<213> ORGANISM: Artificial Sequence
<220> FEATURE:
<223> OTHER INFORMATION: OmpA - syn_evolved - Randomized region - short
      sequence - B16

<400> SEQUENCE: 4
gttcgtatga agaag                                                 15

<210> SEQ ID NO 5
<211> LENGTH: 15
<212> TYPE: DNA
<213> ORGANISM: Artificial Sequence
<220> FEATURE:
<223> OTHER INFORMATION: OmpA - syn_evolved - Randomized region - short
      sequence - B6

<400> SEQUENCE: 5
aaggaaatga agaag                                                 15

<210> SEQ ID NO 6
<211> LENGTH: 15
<212> TYPE: DNA
<213> ORGANISM: Artificial Sequence
<220> FEATURE:
<223> OTHER INFORMATION: OmpA - syn_evolved - Randomized region - short
      sequence - B7

<400> SEQUENCE: 6
aattctatga aaaag                                                 15

<210> SEQ ID NO 7
<211> LENGTH: 15
<212> TYPE: DNA
<213> ORGANISM: Artificial Sequence
<220> FEATURE:
<223> OTHER INFORMATION: PhoA - syn_evolved - Randomized region - short
      sequence - C5

<400> SEQUENCE: 7
```

```
taacgtatga agcaa                                                       15

<210> SEQ ID NO 8
<211> LENGTH: 15
<212> TYPE: DNA
<213> ORGANISM: Artificial Sequence
<220> FEATURE:
<223> OTHER INFORMATION: PhoA - syn_evolved - Randomized region - short
      sequence - C3

<400> SEQUENCE: 8
attatgatga agcaa                                                       15

<210> SEQ ID NO 9
<211> LENGTH: 15
<212> TYPE: DNA
<213> ORGANISM: Artificial Sequence
<220> FEATURE:
<223> OTHER INFORMATION: DsbA - syn_evolved - Randomized region - short
      sequence - D15

<400> SEQUENCE: 9
cgtaggatga aaaag                                                       15

<210> SEQ ID NO 10
<211> LENGTH: 14
<212> TYPE: DNA
<213> ORGANISM: Artificial Sequence
<220> FEATURE:
<223> OTHER INFORMATION: DsbA - syn_evolved - Randomized region - short
      sequence - D2

<400> SEQUENCE: 10
ggtggatgaa gaaa                                                        14

<210> SEQ ID NO 11
<211> LENGTH: 15
<212> TYPE: DNA
<213> ORGANISM: Artificial Sequence
<220> FEATURE:
<223> OTHER INFORMATION: DsbA - syn_evolved - Randomized region - short
      sequence - D11

<400> SEQUENCE: 11
ggctccatga aaaag                                                       15

<210> SEQ ID NO 12
<211> LENGTH: 15
<212> TYPE: DNA
<213> ORGANISM: Artificial Sequence
<220> FEATURE:
<223> OTHER INFORMATION: PelB - syn_evolved - Randomized region - short
      sequence - E5

<400> SEQUENCE: 12
atcaggatga agtat                                                       15

<210> SEQ ID NO 13
<211> LENGTH: 15
<212> TYPE: DNA
<213> ORGANISM: Artificial Sequence
<220> FEATURE:
<223> OTHER INFORMATION: PelB - syn_evolved - Randomized region - short
      sequence - E12

<400> SEQUENCE: 13
tcaagtatga aatat                                                       15
```

-continued

```
<210> SEQ ID NO 14
<211> LENGTH: 15
<212> TYPE: DNA
<213> ORGANISM: Artificial Sequence
<220> FEATURE:
<223> OTHER INFORMATION: PelB - syn_evolved - Randomized region - short
      sequence - E13

<400> SEQUENCE: 14
ctgtttatga aatat                                                       15

<210> SEQ ID NO 15
<211> LENGTH: 51
<212> TYPE: DNA
<213> ORGANISM: Artificial Sequence
<220> FEATURE:
<223> OTHER INFORMATION: MalE - syn_evolved - Randomized region - full
      sequence - A14

<400> SEQUENCE: 15
gtttaacttt aagaaggaga tcgtattatg aaaattaaaa caggtgcacg c              51

<210> SEQ ID NO 16
<211> LENGTH: 51
<212> TYPE: DNA
<213> ORGANISM: Artificial Sequence
<220> FEATURE:
<223> OTHER INFORMATION: MalE - syn_evolved - Randomized region - full
      sequence - A2

<400> SEQUENCE: 16
gtttaacttt aagaaggaga tcatggaatg aagatcaaaa caggtgcacg c              51

<210> SEQ ID NO 17
<211> LENGTH: 51
<212> TYPE: DNA
<213> ORGANISM: Artificial Sequence
<220> FEATURE:
<223> OTHER INFORMATION: MalE - syn_evolved - Randomized region - full
      sequence - A6

<400> SEQUENCE: 17
gtttaacttt aagaaggaga ttagtggatg aaaataaaaa caggtgcacg c              51

<210> SEQ ID NO 18
<211> LENGTH: 51
<212> TYPE: DNA
<213> ORGANISM: Artificial Sequence
<220> FEATURE:
<223> OTHER INFORMATION: OmpA - syn_evolved - Randomized region - full
      sequence - B16

<400> SEQUENCE: 18
gtttaacttt aagaaggaga tgttcgtatg aagaagacag ctatcgcgat t              51

<210> SEQ ID NO 19
<211> LENGTH: 51
<212> TYPE: DNA
<213> ORGANISM: Artificial Sequence
<220> FEATURE:
<223> OTHER INFORMATION: OmpA - syn_evolved - Randomized region - full
      sequence - B6

<400> SEQUENCE: 19
gtttaacttt aagaaggaga taaggaaatg aagaagacag ctatcgcgat t              51
```

-continued

```
<210> SEQ ID NO 20
<211> LENGTH: 51
<212> TYPE: DNA
<213> ORGANISM: Artificial Sequence
<220> FEATURE:
<223> OTHER INFORMATION: OmpA - syn_evolved - Randomized region - full
      sequence - B7

<400> SEQUENCE: 20
gtttaacttt aagaaggaga taattctatg aaaaagacag ctatcgcgat t            51

<210> SEQ ID NO 21
<211> LENGTH: 51
<212> TYPE: DNA
<213> ORGANISM: Artificial Sequence
<220> FEATURE:
<223> OTHER INFORMATION: PhoA - syn_evolved - Randomized region - full
      sequence - C5

<400> SEQUENCE: 21
gtttaacttt aagaaggaga ttaacgtatg aagcaaagca ctattgcact g            51

<210> SEQ ID NO 22
<211> LENGTH: 51
<212> TYPE: DNA
<213> ORGANISM: Artificial Sequence
<220> FEATURE:
<223> OTHER INFORMATION: PhoA - syn_evolved - Randomized region - full
      sequence - C3

<400> SEQUENCE: 22
gtttaacttt aagaaggaga tattatgatg aagcaaagca ctattgcact g            51

<210> SEQ ID NO 23
<211> LENGTH: 51
<212> TYPE: DNA
<213> ORGANISM: Artificial Sequence
<220> FEATURE:
<223> OTHER INFORMATION: DsbA - syn_evolved - Randomized region - full
      sequence - D15

<400> SEQUENCE: 23
gtttaacttt aagaaggaga tcgtaggatg aaaaagattt ggctggcgct g            51

<210> SEQ ID NO 24
<211> LENGTH: 51
<212> TYPE: DNA
<213> ORGANISM: Artificial Sequence
<220> FEATURE:
<223> OTHER INFORMATION: DsbA - syn_evolved - Randomized region - full
      sequence - D2

<400> SEQUENCE: 24
gtttaacttt aagaaggaga tcggtggatg aagaaaattt ggctggcgct g            51

<210> SEQ ID NO 25
<211> LENGTH: 51
<212> TYPE: DNA
<213> ORGANISM: Artificial Sequence
<220> FEATURE:
<223> OTHER INFORMATION: DsbA - syn_evolved - Randomized region - full
      sequence - D11

<400> SEQUENCE: 25
gtttaacttt aagaaggaga tggctccatg aaaaagattt ggctggcgct g            51
```

-continued

```
<210> SEQ ID NO 26
<211> LENGTH: 51
<212> TYPE: DNA
<213> ORGANISM: Artificial Sequence
<220> FEATURE:
<223> OTHER INFORMATION: PelB - syn_evolved - Randomized region - full
      sequence - E5

<400> SEQUENCE: 26
gtttaacttt aagaaggaga tatcaggatg aagtatctgc tgccgaccgc t              51

<210> SEQ ID NO 27
<211> LENGTH: 51
<212> TYPE: DNA
<213> ORGANISM: Artificial Sequence
<220> FEATURE:
<223> OTHER INFORMATION: PelB - syn_evolved - Randomized region - full
      sequence - E12

<400> SEQUENCE: 27
gtttaacttt aagaaggaga ttcaagtatg aaatatctgc tgccgaccgc t              51

<210> SEQ ID NO 28
<211> LENGTH: 51
<212> TYPE: DNA
<213> ORGANISM: Artificial Sequence
<220> FEATURE:
<223> OTHER INFORMATION: PelB - syn_evolved - Randomized region - full
      sequence - E13

<400> SEQUENCE: 28
gtttaacttt aagaaggaga tctgtttatg aaatatctgc tgccgaccgc t              51

<210> SEQ ID NO 29
<211> LENGTH: 26
<212> TYPE: PRT
<213> ORGANISM: Escherichia coli

<400> SEQUENCE: 29

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 30
<211> LENGTH: 21
<212> TYPE: PRT
<213> ORGANISM: Escherichia coli

<400> SEQUENCE: 30

Met Lys Lys Thr Ala Ile Ala Ile Ala Val Ala Leu Ala Gly Phe Ala
1               5                   10                  15

Thr Val Ala Gln Ala
            20

<210> SEQ ID NO 31
<211> LENGTH: 21
<212> TYPE: PRT
<213> ORGANISM: Escherichia coli

<400> SEQUENCE: 31

Met Lys Gln Ser Thr Ile Ala Leu Ala Leu Leu Pro Leu Leu Phe Thr
1               5                   10                  15

Pro Val Thr Lys Ala
            20
```

```
<210> SEQ ID NO 32
<211> LENGTH: 19
<212> TYPE: PRT
<213> ORGANISM: Escherichia coli

<400> SEQUENCE: 32

Met Lys Lys Ile Trp Leu Ala Leu Ala Gly Leu Val Leu Ala Phe Ser
1               5                   10                  15

Ala Ser Ala

<210> SEQ ID NO 33
<211> LENGTH: 22
<212> TYPE: PRT
<213> ORGANISM: Erwinia carotovora

<400> SEQUENCE: 33

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 34
<211> LENGTH: 81
<212> TYPE: DNA
<213> ORGANISM: Artificial Sequence
<220> FEATURE:
<223> OTHER INFORMATION: MalE - SP - DNA sequence - A14

<400> SEQUENCE: 34
atgaaaatta aaacaggtgc acgcatcctc gcattatccg cattaacgac gatgatgttt      60
tccgcctcgg ctctcgccca c                                                81

<210> SEQ ID NO 35
<211> LENGTH: 81
<212> TYPE: DNA
<213> ORGANISM: Artificial Sequence
<220> FEATURE:
<223> OTHER INFORMATION: MalE - SP - DNA sequence - A2

<400> SEQUENCE: 35
atgaagatca aaacaggtgc acgcatcctc gcattatccg cattaacgac gatgatgttt      60
tccgcctcgg ctctcgccca c                                                81

<210> SEQ ID NO 36
<211> LENGTH: 81
<212> TYPE: DNA
<213> ORGANISM: Artificial Sequence
<220> FEATURE:
<223> OTHER INFORMATION: MalE - SP - DNA sequence - A6

<400> SEQUENCE: 36
atgaaaataa aaacaggtgc acgcatcctc gcattatccg cattaacgac gatgatgttt      60
tccgcctcgg ctctcgccca c                                                81

<210> SEQ ID NO 37
<211> LENGTH: 81
<212> TYPE: DNA
<213> ORGANISM: Artificial Sequence
<220> FEATURE:
<223> OTHER INFORMATION: OmpA - SP - DNA sequence - B16

<400> SEQUENCE: 37
```

-continued

```
atgaaaataa aaacaggtgc acgcatcctc gcattatccg cattaacgac gatgatgttt      60
tccgcctcgg ctctcgccca c                                                81

<210> SEQ ID NO 38
<211> LENGTH: 66
<212> TYPE: DNA
<213> ORGANISM: Artificial Sequence
<220> FEATURE:
<223> OTHER INFORMATION: OmpA - SP - DNA sequence - B6

<400> SEQUENCE: 38
atgaagaaga cagctatcgc gattgcagtg gcactggctg gtttcgctac cgtagcgcag      60
gcccac                                                                 66

<210> SEQ ID NO 39
<211> LENGTH: 66
<212> TYPE: DNA
<213> ORGANISM: Artificial Sequence
<220> FEATURE:
<223> OTHER INFORMATION: OmpA - SP - DNA sequence - B7

<400> SEQUENCE: 39
atgaaaaaga cagctatcgc gattgcagtg gcactggctg gtttcgctac cgtagcgcag      60
gcccac                                                                 66

<210> SEQ ID NO 40
<211> LENGTH: 66
<212> TYPE: DNA
<213> ORGANISM: Artificial Sequence
<220> FEATURE:
<223> OTHER INFORMATION: PhoA - SP - DNA sequence - C5

<400> SEQUENCE: 40
atgaagcaaa gcactattgc actggcactc ttaccgttac tgtttacccc tgtgacaaaa      60
gcccac                                                                 66

<210> SEQ ID NO 41
<211> LENGTH: 66
<212> TYPE: DNA
<213> ORGANISM: Artificial Sequence
<220> FEATURE:
<223> OTHER INFORMATION: PhoA - SP - DNA sequence - C3

<400> SEQUENCE: 41
atgaagcaaa gcactattgc actggcactc ttaccgttac tgtttacccc tgtgacaaaa      60
gcccac                                                                 66

<210> SEQ ID NO 42
<211> LENGTH: 60
<212> TYPE: DNA
<213> ORGANISM: Artificial Sequence
<220> FEATURE:
<223> OTHER INFORMATION: DsbA - SP - DNA sequence - D15

<400> SEQUENCE: 42
atgaaaaaga tttggctggc gctggctggt ttagttttag cgtttagcgc atcggcgcac      60

<210> SEQ ID NO 43
<211> LENGTH: 60
<212> TYPE: DNA
<213> ORGANISM: Artificial Sequence
<220> FEATURE:
```

```
<223> OTHER INFORMATION: DsbA - SP - DNA sequence - D2

<400> SEQUENCE: 43
atgaagaaaa tttggctggc gctggctggt ttagtttttag cgtttagcgc atcggcgcac      60

<210> SEQ ID NO 44
<211> LENGTH: 60
<212> TYPE: DNA
<213> ORGANISM: Artificial Sequence
<220> FEATURE:
<223> OTHER INFORMATION: DsbA - SP - DNA sequence - D11

<400> SEQUENCE: 44
atgaaaaaga tttggctggc gctggctggt ttagtttttag cgtttagcgc atcggcgcac      60

<210> SEQ ID NO 45
<211> LENGTH: 69
<212> TYPE: DNA
<213> ORGANISM: Artificial Sequence
<220> FEATURE:
<223> OTHER INFORMATION: PelB - SP - DNA sequence - E5

<400> SEQUENCE: 45
atgaagtatc tgctgccgac cgctgctgct ggtctgctgc tcctcgctgc ccagccggcg      60
atggcccac                                                              69

<210> SEQ ID NO 46
<211> LENGTH: 69
<212> TYPE: DNA
<213> ORGANISM: Artificial Sequence
<220> FEATURE:
<223> OTHER INFORMATION: PelB - SP - DNA sequence - E12

<400> SEQUENCE: 46
atgaaatatc tgctgccgac cgctgctgct ggtctgctgc tcctcgctgc ccagccggcg      60
atggcccac                                                              69

<210> SEQ ID NO 47
<211> LENGTH: 69
<212> TYPE: DNA
<213> ORGANISM: Artificial Sequence
<220> FEATURE:
<223> OTHER INFORMATION: PelB - SP - DNA sequence - E13

<400> SEQUENCE: 47
atgaaatatc tgctgccgac cgctgctgct ggtctgctgc tcctcgctgc ccagccggcg      60
atggcccac                                                              69

<210> SEQ ID NO 48
<211> LENGTH: 15
<212> TYPE: DNA
<213> ORGANISM: Escherichia coli

<400> SEQUENCE: 48
ataccgatga aaata                                                       15

<210> SEQ ID NO 49
<211> LENGTH: 51
<212> TYPE: DNA
<213> ORGANISM: Escherichia coli

<400> SEQUENCE: 49
gtttaacttt aagaaggaga tataccgatg aaaataaaaa caggtgcacg c              51
```

```
<210> SEQ ID NO 50
<211> LENGTH: 15
<212> TYPE: DNA
<213> ORGANISM: Escherichia coli

<400> SEQUENCE: 50
ataccgatga aaaag                                                          15

<210> SEQ ID NO 51
<211> LENGTH: 51
<212> TYPE: DNA
<213> ORGANISM: Escherichia coli

<400> SEQUENCE: 51
gtttaacttt aagaaggaga tataccgatg aaaaagacag ctatcgcgat t                 51

<210> SEQ ID NO 52
<211> LENGTH: 15
<212> TYPE: DNA
<213> ORGANISM: Escherichia coli

<400> SEQUENCE: 52
ataccgatga aacaa                                                         15

<210> SEQ ID NO 53
<211> LENGTH: 51
<212> TYPE: DNA
<213> ORGANISM: Escherichia coli

<400> SEQUENCE: 53
gtttaacttt aagaaggaga tataccgatg aaacaaagca ctattgcact g                 51

<210> SEQ ID NO 54
<211> LENGTH: 15
<212> TYPE: DNA
<213> ORGANISM: Escherichia coli

<400> SEQUENCE: 54
ataccgatga aaaag                                                          15

<210> SEQ ID NO 55
<211> LENGTH: 51
<212> TYPE: DNA
<213> ORGANISM: Escherichia coli

<400> SEQUENCE: 55
gtttaacttt aagaaggaga tataccgatg aaaaagattt ggctggcgct g                 51

<210> SEQ ID NO 56
<211> LENGTH: 15
<212> TYPE: DNA
<213> ORGANISM: Erwinia carotovora

<400> SEQUENCE: 56
ataccgatga aatac                                                         15

<210> SEQ ID NO 57
<211> LENGTH: 51
<212> TYPE: DNA
<213> ORGANISM: Erwinia carotovora

<400> SEQUENCE: 57
```
gtttaacttt aagaaggaga tataccgatg aaataccctgc tgccgaccgc t          51

<210> SEQ ID NO 58
<211> LENGTH: 81
<212> TYPE: DNA
<213> ORGANISM: Artificial Sequence
<220> FEATURE:
<223> OTHER INFORMATION: MalE - SP - unevolved - DNA sequence

<400> SEQUENCE: 58
atgaaaataa aaacaggtgc acgcatcctc gcattatccg cattaacgac gatgatgttt          60
tccgcctcgg ctctcgccca c          81

<210> SEQ ID NO 59
<211> LENGTH: 66
<212> TYPE: DNA
<213> ORGANISM: Artificial Sequence
<220> FEATURE:
<223> OTHER INFORMATION: OmpA - SP - unevolved - DNA sequence

<400> SEQUENCE: 59
atgaaaaaga cagctatcgc gattgcagtg gcactggctg gtttcgctac cgtagcgcag          60
gcccac          66

<210> SEQ ID NO 60
<211> LENGTH: 66
<212> TYPE: DNA
<213> ORGANISM: Artificial Sequence
<220> FEATURE:
<223> OTHER INFORMATION: PhoA - SP - unevolved - DNA sequence

<400> SEQUENCE: 60
atgaaacaaa gcactattgc actggcactc ttaccgttac tgtttacccc tgtgacaaaa          60
gcccac          66

<210> SEQ ID NO 61
<211> LENGTH: 60
<212> TYPE: DNA
<213> ORGANISM: Artificial Sequence
<220> FEATURE:
<223> OTHER INFORMATION: DsbA - SP - unevolved - DNA sequence

<400> SEQUENCE: 61
atgaaaaaga tttggctggc gctggctggt ttagttttag cgtttagcgc atcggcgcac          60

<210> SEQ ID NO 62
<211> LENGTH: 69
<212> TYPE: DNA
<213> ORGANISM: Artificial Sequence
<220> FEATURE:
<223> OTHER INFORMATION: PelB - SP - unevolved - DNA sequence

<400> SEQUENCE: 62
atgaaatacc tgctgccgac cgctgctgct ggtctgctgc tcctcgctgc ccagccggcg          60
atggcccac          69

SYNTHETICALLY EVOLVED DNA CONSTRUCTS FOR REGULATING SIGNAL PEPTIDE PERFORMANCE AS WELL AS VECTORS, HOST CELLS AND RECOMBINANT PROTEINS THEREOF

INCORPORATION BY REFERENCE OF SEQUENCE LISTING

The sequence listing in an XML, named as 41047_SubstituteSequenceListing_txt of 15 KB, created on Sep. 12, 2023, and submitted to the United States Patent and Trademark Office via e-business website, is incorporated herein by reference.

TECHNICAL FIELD

The present invention relates to the general field of regulating signal peptide performance. More specifically, the present invention relates to regulating recombinant protein expression via controlling signal peptide performance.

BACKGROUND

Bacterial cell factories are widely used in the biotech and pharmaceutical industries for the production of high-value recombinant proteins. Classic examples include industrial enzymes, hormones and antibody fragments, which generate billions of dollars in revenue annually [1,2]. These recombinant proteins are typically engineered with an N-terminal signal peptide so that they will be secreted out of the bacterial cytoplasm [3]. For industrial enzymes, which are usually produced in gram-positive bacteria such as *Bacillus subtilis*, secretion from the cytoplasm to the culture supernatant simplifies purification and downstream processing. For hormones and antibody fragments, which are usually produced in gram-negative bacteria like *Escherichia coli*, secretion from the cytoplasm to the oxidizing environment of the periplasm is necessary for the formation of disulfide bonds that are essential for protein folding and activity [4,5].

Secretion out of the bacterial cytoplasm is usually mediated by the general secretion pore (Sec) [6,7]. Sec is a major hub for protein trafficking as it inserts proteins into the cytoplasmic membrane, and secretes proteins to the envelope and beyond. Secreted proteins are typically targeted to Sec by an N-terminal signal peptide. Signal peptides vary in length and amino acid sequence, but have a distinctive tripartite structure that includes a positively-charged N-terminal region, a hydrophobic core, and a polar C-terminal cleavage site that typically contains the signal peptidase recognition site (Ala-X-Ala) [8,9]. They also have a distinctive codon usage, which includes a biased use of the AAA (Lys) codon at the second position, and a high frequency of non-optimal codons [10-14]. It has been suggested that the signal peptide slows folding of the protein in the cytoplasm and targets it to Sec in a predominantly unfolded confirmation [15]. Upon arrival at Sec the signal peptide also promotes binding to the SecA chaperone, thereby allosterically activating Sec for protein secretion [16]. Given these multiple roles it is likely that signal peptides have co-evolved with the protein that they translocate, as well as with the secretion machinery.

Signal peptides have unpredictable effects on the production yields of recombinant proteins. For example, a signal peptide that supports a high-level of protein synthesis and secretion for one recombinant protein often supports a low-level of protein synthesis and secretion for another.

Herein we refer to this phenomenon as signal peptide performance (i.e. signal peptide strength). Since it is not possible to predict how well a signal peptide will perform with a given recombinant protein, it is common practice to screen large signal peptide-libraries for one that supports a high-level of protein synthesis and secretion [3]. This approach is both time-consuming and expensive. Hence, there is a need for a molecular understanding of signal peptide performance since as it could lead to new methods for (1) identifying suitable signal peptides, and (2) rationally engineering signal peptides that increase production yields in bacterial cell factories.

Translation initiation is a rate-limiting step of protein synthesis in bacteria [17-21], where the 30S subunit of the ribosome, together with the initiation factors IF1 and IF3 bind to the Translation Initiation Region (TIR) of the mRNA. This pre-initiation complex then recruits the GTP bound initiation factor IF2 and the initiating formyl-methionine tRNAfMet. Once assembled, GTP is hydrolyzed, the initiation factors are released and the 50S subunit is recruited [22]. The efficiency of translation initiation is dependent on the nucleotide sequence of the TIR, a stretch of approximately thirty nucleotides that extends from the Shine-Dalgarno region to the fifth codon of the coding sequence (i.e. the first ribosomal footprint) [23]. The TIR is the only variable element during translation. If all possible sequence permutations are considered, there are more than a quintillion TIRs (i.e. $430 > 1 \times 10^{18}$). However only a small number of TIRs are present in bacterial cells and they contain some distinctive sequence features. The most obvious is the Shine-Dalgarno (SD) sequence, a purine rich stretch of 4-9 nucleotides that hydrogen bonds with the 16S rRNA of the 30S subunit 24. This sequence guides the ribosome to the start codon, which is typically an AUG [25]. The start codon is separated from the SD sequence by a spacer region that is typically 9 nucleotides long in *E. coli* [26]. The 5' end of the coding sequence (~15 nucleotides) is also considered to be within the TIR and often harbors rare codons [28,29]. Native bacterial TIRs have co-evolved with the ribosome and are less likely to form mRNA structures compared to the rest of the coding sequence [30,31]. This is thought to promote accessibility of the 30S subunit during translation initiation [28,29,32,33].

DNA constructs relating to signal peptides are known from U.S. Pat. No. 8,361,744. However, the 42 DNA constructs disclosed in U.S. Pat. No. 8,361,744 differ significantly from the DNA constructs of the present invention both with respect to DNA sequence as well as the performance of the signal peptides. Moreover, the DNA constructs of U.S. Pat. No. 8,361,744 have not been synthetically evolved and therefore do not exhibit the technical effects of the DNA constructs disclosed in the present invention.

OBJECT OF INVENTION

The object of the invention is to controlling signal peptide performance.

A further object of the invention is to control recombinant protein expression via controlling signal peptide performance.

A further object of the invention is to increase (i.e. up-regulate) or to decrease (i.e. down-regulate) signal peptide performance.

A further object of the invention is to provide a simple and inexpensive system of DNA constructs, expression vectors and host cells for increasing the production yields of single chain antibody fragments, hormones and other recombinant proteins.

SUMMARY OF THE INVENTION

In the present invention, the inventors have solved the problem and anomaly in recombinant expression plasmid typically used to produce secreted proteins. It is in the art a common practice to place the coding sequence of the signal peptide downstream of the vector encoded 5'UTR. Hence, the resulting TIR is a fusion of the 5'UTR and the first 5 codons of the signal peptide in the TIR. The inventors hypothesized that such a TIR would not function optimally as it had not co-evolved with the ribosome. To test this hypothesis, as described in detail in the DETAILED DESCRIPTION of the present specification, the inventors synthetically evolved the TIR in the presence of host cell ribosomes. The experimental results discussed in the EXAMPLES section of the present specification clearly indicate that the performance of all signal peptides can be improved by synthetic evolution. The most striking example was PelB$^{SP}$, which was initially the worst performing signal peptide for production of β-lactamase, but the best performing following synthetic evolution of the TIR. Thus, in summary, the performance of the signal peptide is largely coupled to the efficiency of translation initiation. The present invention provides a molecular understanding of this signal peptide performance. More importantly, the present invention provides a simple and inexpensive system comprising:

DNA constructs,
expression vectors,
host cells, and
methods of production, for increasing the production yields of single chain antibody fragments, hormones and other recombinant proteins.

The objects of the invention are attained by the subject-matter disclosed in the claims as well as the subject-matter disclosed in the below aspects of the invention.

A first aspect of the invention relates to a DNA construct suitable for controlling signal peptide performance, wherein said DNA construct comprises:

a. a Shine-Dalgarno sequence;
b. an ATG start codon;
c. a sequence of one of SEQ ID 1-28 comprising said ATG start codon; and
d. a signal peptide encoding sequence, wherein said sequence of one of SEQ ID 1-28 comprises at least the first 9 nucleotides of said signal peptide encoding sequence.

In a preferred embodiment, said signal peptide encoding sequence comprises a sequence for expressing a signal peptide selected from MalE (maltose-binding protein precursor), OmpA (outer membrane protein A precursor), PhoA (alkaline phosphatase precursor), DsbA (thiol:disulfide interchange protein), and PelB (periplasmic pectate lyase).

In a preferred embodiment, said signal peptide encoding sequence is a sequence of one of SEQ ID 34-47.

In a preferred embodiment, said signal peptide encoding sequence expresses a signal peptide of a sequence of one of SEQ ID 29-33.

In a preferred embodiment, said Shine-Dalgarno sequences comprises nucleotide sequence TAAGAAGG in the direction of transcription.

In a preferred embodiment, said DNA construct comprise a sequence of one of SEQ ID 15-28, wherein said sequence of one of SEQ ID 15-28 comprises said Shine-Dalgarno sequence, said sequence of one of SEQ ID 1-14 and at least the first 24 nucleotides of said signal peptide encoding sequence.

In a preferred embodiment, said DNA construct is characterized in that:

a sequence of one of SEQ ID 1, 2 and 3 comprises the first 9 nucleotides of a MalE signal peptide encoding sequence of one of SEQ ID 34, 35 and 36, respectively;

a sequence of one of SEQ ID 15, 16 and 17 comprises the first 24 nucleotides of a MalE signal peptide encoding sequence of one of SEQ ID 34, 35 and 36, respectively;

a sequence of one SEQ ID 4, 5 and 6 comprises the first 9 nucleotides of an OmpA signal peptide encoding sequence of one of SEQ ID 37, 38 and 39, respectively;

a sequence of one SEQ ID 18, 19 and 20 comprises the first 24 nucleotides of an OmpA signal peptide encoding sequence of one of SEQ ID 37, 38 and 39, respectively;

a sequence of one SEQ ID 7 and 8 comprises the first 9 nucleotides of a PhoA signal peptide encoding sequence of one of SEQ ID 40 and 41, respectively;

a sequence of one SEQ ID 21 and 22 comprises the first 24 nucleotides of a PhoA signal peptide encoding sequence of one of SEQ ID 40 and 41, respectively;

a sequence of one SEQ ID 9, 10 and 11 comprises the first 9 nucleotides of a DsbA signal peptide encoding sequence of one of SEQ ID 42, 43 and 44, respectively;

a sequence of one SEQ ID 23, 24 and 25 comprises the first 24 nucleotides of a DsbA signal peptide encoding sequence of one of SEQ ID 42, 43 and 44, respectively;

a sequence of one SEQ ID 12, 13 and 14 comprises the first 9 nucleotides of a PelB signal peptide encoding sequence of one of SEQ ID 45, 46 and 47, respectively; and/or a sequence of one SEQ ID 26, 27 and 28 comprises the first 24 nucleotides of a PelB signal peptide encoding sequence of one of SEQ ID 45, 46 and 47, respectively.

In a preferred embodiment, said DNA construct is characterized in that:

said MalE signal peptide encoding sequence of one of SEQ ID 34, 35 and 36 expresses a signal peptide of a sequence of one of SEQ ID 29;

said OmpA signal peptide encoding sequence of one of SEQ ID 37, 38 and 39 expresses a signal peptide of a sequence of one of SEQ ID 30;

said PhoA signal peptide encoding sequence of one of SEQ ID 40 and 41 expresses a signal peptide of a sequence of one of SEQ ID 31;

said DsbA signal peptide encoding sequence of one of SEQ ID 42, 43 and 44 expresses a signal peptide of a sequence of one of SEQ ID 32; and/or said PelB signal peptide encoding sequence of one of SEQ ID 45, 46 and 47 expresses a signal peptide of a sequence of one of SEQ ID 33.

In a preferred embodiment, said DNA construct comprise a sequence of one of SEQ ID 15, 18, 21, 23 and 26.

In a preferred embodiment, said DNA construct is a synthetically evolved DNA construct.

In a preferred embodiment, said DNA construct further comprises a recombinant protein encoding sequence.

A second aspect of the invention relates to a DNA construct suitable for controlling signal peptide performance, wherein said DNA construct comprises a sequence of one of SEQ ID 15-28.

In a preferred embodiment, said DNA construct also comprises a signal peptide encoding sequence.

In a preferred embodiment, said signal peptide encoding sequence comprises a sequence for expressing a signal peptide selected from MalE (maltose-binding protein precursor), OmpA (outer membrane protein A precursor), PhoA (alkaline phosphatase precursor), DsbA (thiol:disulfide interchange protein), and PelB (periplasmic pectate lyase).

In a preferred embodiment, said sequence of one of SEQ ID 15-28 comprises the first 24 nucleotides of said signal peptide encoding sequence.

In a preferred embodiment, said signal peptide encoding sequence is a sequence of one of SEQ ID 34-47.

In a preferred embodiment, said signal peptide encoding sequence expresses a signal peptide of a sequence of one of SEQ ID 29-33.

In a preferred embodiment, said DNA construct is characterized in that:

a sequence of one of SEQ ID 15, 16 and 17 comprises the first 24 nucleotides of a MalE signal peptide encoding sequence of one of SEQ ID 34, 35 and 36, respectively;

a sequence of one SEQ ID 18, 19 and 20 comprises the first 24 nucleotides of an OmpA signal peptide encoding sequence of one of SEQ ID 37, 38 and 39, respectively;

a sequence of one SEQ ID 21 and 22 comprises the first 24 nucleotides of a PhoA signal peptide encoding sequence of one of SEQ ID 40 and 41, respectively;

a sequence of one SEQ ID 23, 24 and 25 comprises the first 24 nucleotides of a DsbA signal peptide encoding sequence of one of SEQ ID 42, 43 and 44, respectively; and/or a sequence of one SEQ ID 26, 27 and 28 comprises the first 24 nucleotides of a PelB signal peptide encoding sequence of one of SEQ ID 45, 46 and 47, respectively.

In a preferred embodiment, said DNA construct is characterized in that:

said MalE signal peptide encoding sequence of one of SEQ ID 34, 35 and 36 expresses a signal peptide of a sequence of one of SEQ ID 29;

said OmpA signal peptide encoding sequence of one of SEQ ID 37, 38 and 39 expresses a signal peptide of a sequence of one of SEQ ID 30;

said PhoA signal peptide encoding sequence of one of SEQ ID 40 and 41 expresses a signal peptide of a sequence of one of SEQ ID 31;

said DsbA signal peptide encoding sequence of one of SEQ ID 42, 43 and 44 expresses a signal peptide of a sequence of one of SEQ ID 32; and/or said PelB signal peptide encoding sequence of one of SEQ ID 45, 46 and 47 expresses a signal peptide of a sequence of one of SEQ ID 33.

In a preferred embodiment, said DNA construct comprises a sequence of one of SEQ ID 15, 18, 21, 23 and 26.

In a preferred embodiment, said DNA construct is a synthetically evolved DNA construct.

In a preferred embodiment, said DNA construct further comprises a recombinant protein encoding sequence.

A third aspect of the invention relates to a DNA construct suitable for controlling signal peptide performance, wherein said DNA construct comprises a sequence of one of SEQ ID 49, 51, 53, 55 and 57.

In a preferred embodiment, said DNA construct also comprises a signal peptide encoding sequence.

In a preferred embodiment, said signal peptide encoding sequence comprises a sequence for expressing a signal peptide selected from MalE (maltose-binding protein precursor), OmpA (outer membrane protein A precursor), PhoA (alkaline phosphatase precursor), DsbA (thiol:disulfide interchange protein), and Pelb (periplasmic pectate lyase).

In a preferred embodiment, said signal peptide encoding sequence is a sequence of one of SEQ ID 58-62.

In a preferred embodiment, said signal peptide encoding sequence expresses a signal peptide of a sequence of one of SEQ ID 29-33.

In a preferred embodiment, said DNA construct is characterized in that:

a sequence of SEQ ID 49 comprises the first 24 nucleotides of a MalE signal peptide encoding sequence of SEQ ID 58;

a sequence of SEQ ID 51 comprises the first 24 nucleotides of an OmpA signal peptide encoding sequence of SEQ ID 59;

a sequence of SEQ ID 53 comprises the first 24 nucleotides of a PhoA signal peptide encoding sequence of SEQ ID 60;

a sequence of SEQ ID 55 comprises the first 24 nucleotides of a DsbA signal peptide encoding sequence of SEQ ID 61; and/or a sequence of SEQ ID 57 comprises the first 24 nucleotides of a PelB signal peptide encoding sequence of SEQ ID 62.

In a preferred embodiment, said DNA construct is characterized in that:

said MalE signal peptide encoding sequence of SEQ ID 58 expresses a signal peptide of sequence of SEQ ID 29;

said OmpA signal peptide encoding sequence of SEQ ID 59 expresses a signal peptide of sequence of SEQ ID 30;

said PhoA signal peptide encoding sequence of SEQ ID 60 expresses a signal peptide of sequence of SEQ ID 31;

said DsbA signal peptide encoding sequence of SEQ ID 61 expresses a signal peptide of sequence SEQ ID 32; and/or said PelB signal peptide encoding sequence of SEQ ID 62 expresses a signal peptide of a sequence of one of SEQ ID 3.

In a preferred embodiment, said DNA construct further comprises a recombinant protein encoding sequence.

A fourth aspect of the invention relates to an expression vector comprising a DNA construct according to the above disclosed first, second or third aspects of the invention, wherein the expression vector is preferably a plasmid, more preferably PET expression vector, and most preferably pet28A A fifth aspect of the invention relates to a host cell comprising the above disclosed expression vector of the fourth aspect of the invention, wherein said host cell is preferably a bacterial cell, more preferably said bacterial cell is *E. coli* and most preferably *E. coli* strain BL21(DE3) pLysS.

A sixth aspect of the invention relates to a recombinant protein expressed by the above disclosed host cell of the fifth aspect of the invention.

A seventh aspect of the invention relates to a method of expressing the above disclosed recombinant protein of the sixth aspect of the invention, said method comprising the steps of:

introducing said DNA construct according to the above disclosed first, second or third aspects of the invention into an expression vector;

introducing the expression into a host cell;

growing the host cell; and and recovering the recombinant protein from the host cell.

An eighth aspect of the invention relates to an RNA molecule expressed by a DNA construct according to the above disclosed first, second or third aspects of the invention.

DETAILED DESCRIPTION

Figure 1:
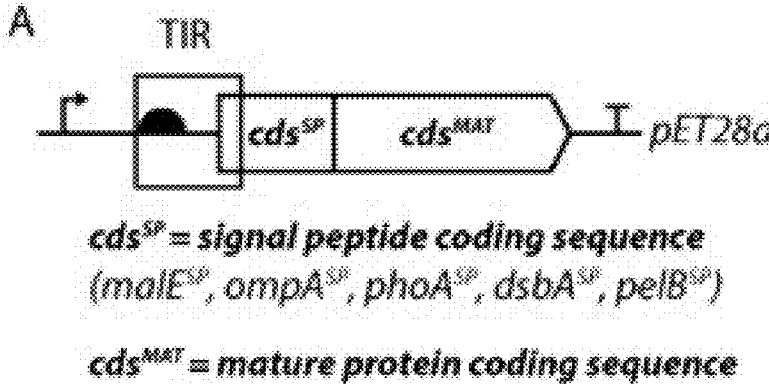
FIG. 1. A comparison of commonly used signal peptides. (A) An overview of the expression cassettes used in this experiment. The TIR region represented by the boxed area, from the Shine-Dalgarno to the fifth codon of the signal sequence. The coding sequences for five commonly used signal peptides (MalE$^{SP}$, OmpA$^{SP}$, PhoA$^{SP}$, DsbA$^{SP}$, PelB$^{SP}$) were cloned into the pET28a vector, upstream of the mature coding sequences for β-lactamase, scFv$^{HER2}$ or FtYfgM$^{45-170}$. Protein production was induced for two hours, then a volume of cells corresponding to 0.2 OD$_{600}$ units of cells were harvested, separated by a 12% SDS-PAGE and protein levels determined by immuno-blotting with antisera to β-lactamase (B), or the poly-Histidine tag of scFv$^{HER2}$ (C) and FtYfgM$^{45-170}$ (D). To ensure that protein loading was consistent between the samples, the membranes were stained with Amido black after immuno-detection. 'Pre' denotes the precursor form of the protein, which contains the signal sequence and is presumed to be in the cytoplasm. 'Mat' precursor denotes the mature form, which is presumed to be in the periplasm as the signal peptide has been cleaved.
Figure 1:
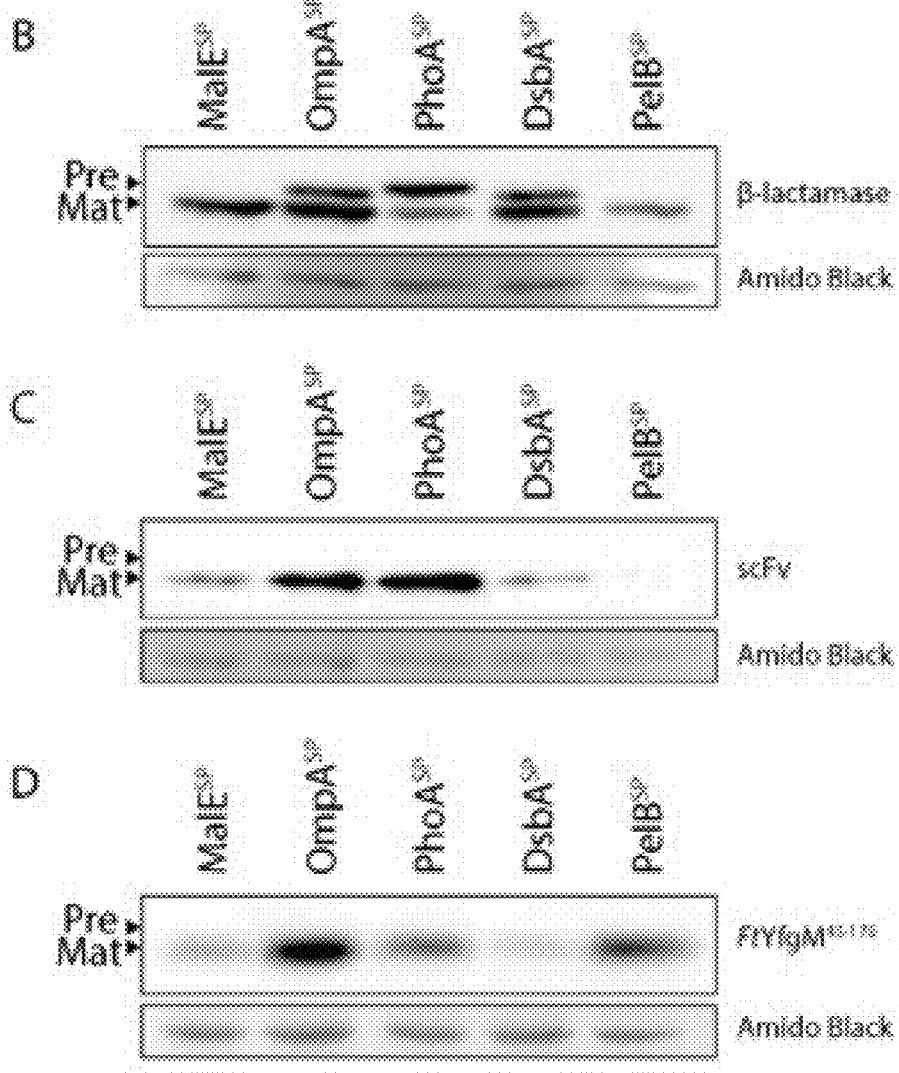

The present invention relates to controlling signal peptide performance with a DNA construct wherein the DNA construct comprises:

e. a Shine-Dalgarno sequence, f. an ATG start codon, g. a sequence of one of SEQ ID 1-28 comprising said ATG start codon, and h. a signal peptide encoding sequence, wherein the sequence of one of SEQ ID 1-28 comprises at least the first 9 nucleotides of the signal peptide encoding sequence. When the DNA construct comprise a sequence of one of SEQ ID 15-28 then such a sequence comprises the Shine-Dalgarno sequence, said sequence of one of SEQ ID 1-14 and at least the first 24 nucleotides of the signal peptide encoding sequence.

The signal peptide encoding sequence may comprises a sequence for expressing a signal peptide selected from MalE, OmpA, PhoA, DsbA and PelB. A specific signal peptide encoding sequence may be a sequence of one of SEQ ID 34-47 which may express a signal peptide of a sequence of one of SEQ ID 29-33 indicated in Table 1.

However, DNA constructs comprising a sequence of one of SEQ ID 48-57 may also be used.

The preferred combinations of (a) a DNA construct sequence, (b) a signal peptide sequence, and/or (c) a signal peptide DNA sequence, are disclosed in Tables 1 and 2.

TABLE 1

Signal peptides and their corresponding peptide and DNA sequences.
Several peptide DNA sequences may express the same peptide
sequence due to the synonymous codon changes discussed in
Example 2, FIG. 2 and elsewhere in the specification.

| Signal peptide | Peptide Sequence | Seq ID | DNA sequence | Seq ID |
|---|---|---|---|---|
| MalE$^{SP}$ | MKIKTGARILALSALTTMMFSA SALA | 29 | ATGAAAATAAAAACAGG TGCACGCATCCTCGCATT ATCCGCATTAACGACGAT GATGTTTTCCGCCTCGGC TCTCGCCCAC | 58 |
| | | | ATGAAAATTAAAACAGGT GCACGCATCCTCGCATTA ATGTCCGCATTAACGACG ATGATGTTTTCCGCCTCG GCTCTCGCCCAC | 34 |
| | | | ATGAAGATCAAAACAGG TGCACGCATCCTCGCATT ATCCGCATTAACGACGAT GATGTTTTCCGCCTCGGC TCTCGCCCAC | 35 |
| | | | ATGAAAATAAAAACAGG TGCACGCATCCTCGCATT ATCCGCATTAACGACGAT GATGTTTTCCGCCTCGGC TCTCGCCCAC | 36 |
| OmpA$^{SP}$ | MKKTAIAIAVALAGFATVAQA | 30 | ATGAAAAAGACAGCTATC GCGATTGCAGTGGCACTG GCTGGTTTCGCTACCGTA GCGCAGGCCCAC | 59 |
| | | | ATGAAGAAGACAGCTATC GCGATTGCAGTGGCACTG GCTGGTTTCGCTACCGTA GCGCAGGCCCAC | 37 |
| | | | ATGAAGAAGACAGCTATC GCGATTGCAGTGGCACTG GCTGGTTTCGCTACCGTA GCGCAGGCCCAC | 38 |
| | | | ATGAAAAAGACAGCTATC GCGATTGCAGTGGCACTG GCTGGTTTCGCTACCGTA GCGCAGGCCCAC | 39 |
| PhoA$^{SP}$ | MKQSTIALALLPLLFTPVTKA | 31 | ATGAAACAAAGCACTATT GCACTGGCACTCTTACCG TTACTGTTTACCCCTGTG ACAAAAGCCCAC | 60 |
| | | | ATGAAGCAAAGCACTATT GCACTGGCACTCTTACCG TTACTGTTTACCCCTGTG ACAAAAGCCCAC | 40 |
| | | | ATGAAGCAAAGCACTATT GCACTGGCACTCTTACCG TTACTGTTTACCCCTGTG ACAAAAGCCCAC | 41 |
| DsbA$^{SP}$ | MKKIWLALAGLVLAFSASA | 32 | ATGAAAAAGATTTGGCTG GCGCTGGCTGGTTTAGTT TTAGCGTTTAGCGCATCG GCGCAC | 61 |
| | | | ATGAAAAAGATTTGGCTG GCGCTGGCTGGTTTAGTT TTAGCGTTTAGCGCATCG GCGCAC | 42 |
| | | | ATGAAGAAATTTGGCTG GCGCTGGCTGGTTTAGTT TTAGCGTTTAGCGCATCG GCGCAC | 43 |

TABLE 1-continued

Signal peptides and their corresponding peptide and DNA sequences.
Several peptide DNA sequences may express the same peptide
sequence due to the synonymous codon changes discussed in
Example 2, FIG. 2 and elsewhere in the specification.

| Signal peptide | Peptide Sequence | Seq ID | DNA sequence | Seq ID |
|---|---|---|---|---|
| | | | ATGAAAAAGATTTGGCTG GCGCTGGCTGGTTTAGTT TTAGCGTTTAGCGCATCG GCGCAC | 44 |
| PelB$^{SP}$ | MKYLLPTAAAGLLLLAAQPAM A | 33 | ATGAAATACCTGCTGCCG ACCGCTGCTGCTGGTCTG CTGCTCCTCGCTGCCCAG CCGGCGATGGCCCAC | 62 |
| | | | ATGAAGTATCTGCTGCCG ACCGCTGCTGCTGGTCTG CTGCTCCTCGCTGCCCAG CCGGCGATGGCCCAC | 45 |
| | | | ATGAAATATCTGCTGCCG ACCGCTGCTGCTGGTCTG CTGCTCCTCGCTGCCCAG CCGGCGATGGCCCAC | 46 |
| | | | ATGAAATATCTGCTGCCG ACCGCTGCTGCTGGTCTG CTGCTCCTCGCTGCCCAG CCGGCGATGGCCCAC | 47 |

The invention further relates to an expression vector comprising the above-mentioned DNA construct. Additionally, the present invention relates to host cell comprising said expression vector. Furthermore, the present invention relates to a recombinant protein expressed by said host cell as well as a method for expressing said recombinant protein. The DNA construct may further comprise a recombinant protein encoding sequence.

The above described DNA constructs, expression vectors, host cell and recombinant proteins have been described in the EXAMPLES and EXPERIMENTAL PROCEDURES sections of this specification. Moreover, the results of the comparative tests are discussed in the EXAMPLES section to provide evidence of the increased (i.e. up-regulated) signal peptide performance of DNA constructs comprising a sequence of one of SEQ ID 1-28. However, the present invention may alternatively be used for decreasing the signal peptide performance of DNA constructs comprising a sequence of one of SEQ ID 48-57; such an effect may be relevant in cases when the expression of recombinant protein needs to be down-regulated.

Some of the significant comparative tests discussed in the EXAMPLES are summarized in the following paragraphs before the EXAMPLES section.

As already indicated, the present invention relates to improving signal peptide performance by synthetically evolving the TIR. The present invention further provides a simple and inexpensive solution for increasing the production yields of secreted proteins in bacterial cell factories. Moreover, the present invention will be compatible with other published methods; such as those that use titratable promoters to tune transcription rates of secreted proteins [40]. A potential problem is the need for screening of large TIR$^{LIBRARIES}$. However, in the present invention, said problem was solved by using β-lactamase protein, which confers resistance to β-lactam antibiotics and can be easily screened; this embodiment of the present invention is discussed in detail in Examples 2 and 3. For proteins where no simple screening assay is available it is possible to translationallycouple β-lactamase to the recombinant protein and thereby solve potential problems. It is also possible to use the signal peptides in pET28a vectors from the present invention, which possess a TIR$^{SYN\_EVOLVED}$ and which improved production yields of a single chain antibody fragment, a hormone and another recombinant protein in *Escherichia coli*; this embodiment of the invention is discussed in detail in Example 4

A link between signal peptide performance and the efficiency of translation initiation has been implied previously. Punginelli and co-workers noted that non-synonymous nucleotide changes in the signal peptide of the Tat-dependent formate dehydrogenase increased production levels by up to 60-fold in *E. coli* [38]. And Ng and Sarkar noted that synonymous changes to the Usp45sp signal peptide in *Lactococcus lactis* helped to increase production levels of a nuclease and an amylase by approximately 15% [39]. Both studies postulated that the nucleotide changes helped to relax mRNA structure that had sequestered the TIR.

The present invention also demonstrates that nucleotide changes in the TIR can influence production of secreted proteins (although this could not be correlated to changes in mRNA structure). Significantly, the present invention goes beyond the current literature as indicated in the comparative experiments described in Example 2 and FIG. 2 which demonstrate that signal peptides generally under-perform in protein production experiments because the TIR, encompassing the 5' UTR of the plasmid and the 5' terminus of the gene coding sequence, has not co-evolved with the ribosomes of the host cell.

Figure 2:
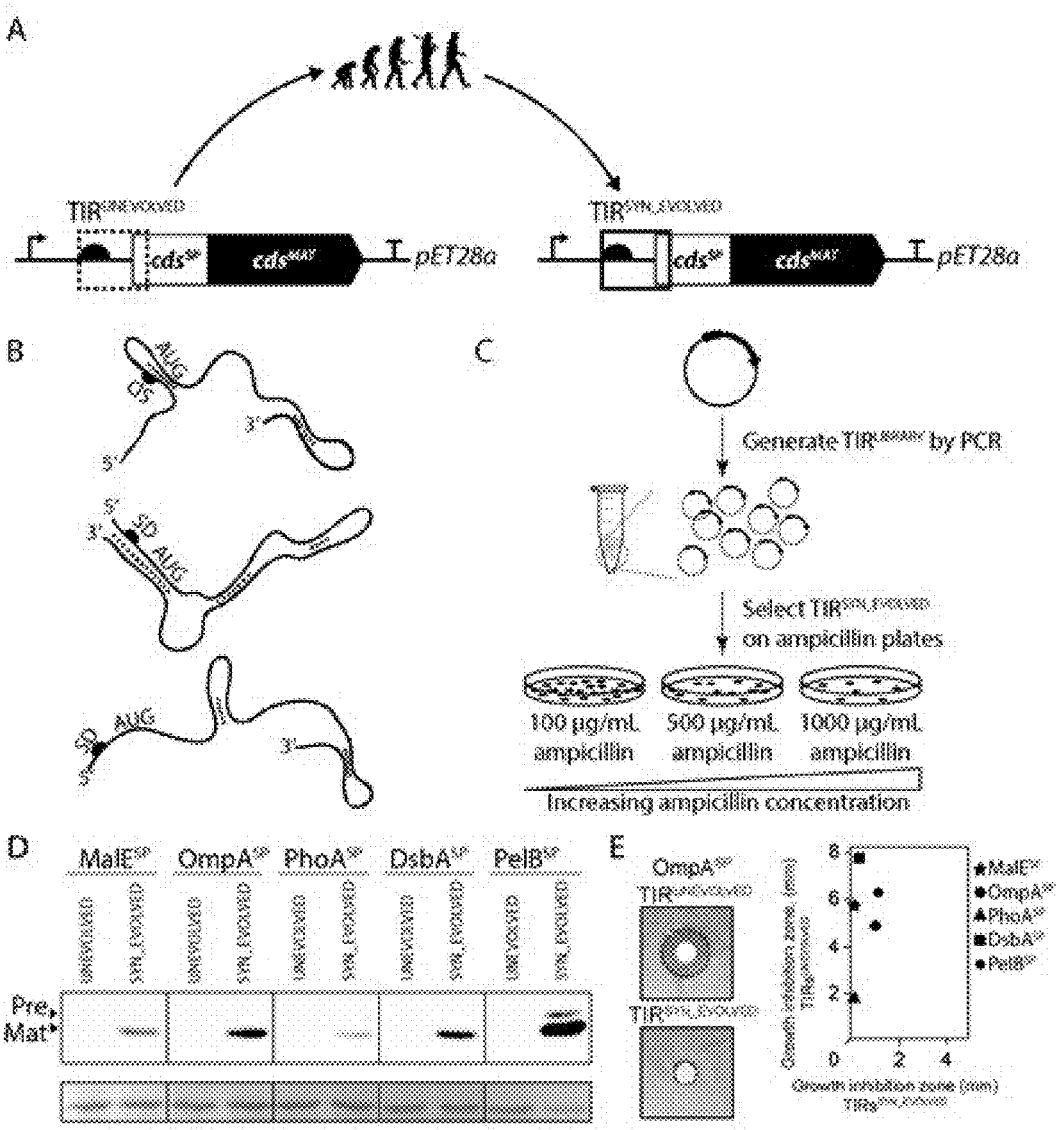
FIG. 2. Improved signal peptide performance following synthetic evolution of the TIR (A) A synthetic evolution approach was used to convert a TIR$^{UNEVOLVED}$ to a TIR$^{SYN\_EVOLVED}$. The TIR is defined as the region from the Shine-Dalgarno (half-dome) to codon 5 of the signal peptide. (B) mRNA has a high propensity to form structures, thus a TIR$^{UNEVOLVED}$ can be sequestered into short-(top) or long-range structures (middle). Synthetic evolution should select a TIR$^{SYN\_EVOLVED}$ that is relaxed and more accessible to the ribosome (bottom). (C) An overview of the synthetic evolution process. A TIR$^{LIBRARY}$ was constructed by completely randomising the six nucleotides immediately upstream of the AUG start codon, and partially randomising the six nucleotides immediately downstream of the AUG start codon (allowing synonymous codons changes only). The TIR$^{LIBRARY}$ was transformed into E. coli BL21(DE3) pLysS and plated on increasing concentrations of ampicillin. A TIR$^{SYN\_EVOLVED}$ was identified on the plate containing the highest concentration of ampicillin relative to the TIR$^{UNEVOLVED}$ variant. (D) β-lactamase production levels from TIR$^{UNEVOLVED}$/TIR$^{SYN\_EVOLVED}$ pairs were assessed by immuno-blotting. In this experiment, β-lactamase production was induced for two hours, then a volume of cells corresponding to 0.2 OD$_{600}$ units of cells were harvested, separated by a 12% SDS-PAGE and protein levels were determined by immuno-blotting with antisera to β-lactamase. To ensure that protein loading was consistent between the samples, the membrane was stained with Amido black after immuno-detection. 'Pre' denotes the precursor form of the protein, which contains the signal peptide fused version of β-lactamase, which we presume to be in the cytoplasm as the signal peptide is still present. 'Mat' precursor denotes the mature version of β-lactamase, which presumably is in the periplasm as the signal peptide has been cleaved. (E) β-lactamase activity from TIR$^{UNEVOLVED}$/TIR$^{SYN\_EVOLVED}$ pairs was assessed using the disc diffusion assay. Here a filter disc containing 2 mg of ampicillin was placed on top of an LB-agar plate containing a lawn of bacteria expressing β-lactamase from either a TIR$^{UNEVOLVED}$ or a TIR$^{SYN\_EVOLVED}$. The diameter of the growth-inhibition zone was measured for each experiment. In all cases, a TIR$^{SYN\_EVOLVED}$ conferred more resistant to ampicillin than TIR$^{UNEVOLVED}$.

As further disclosed in Example 2 and FIG. 2, the inventors were able to support this molecular explanation by demonstrating that a synthetic evolution process could improve the performance of all commonly used signal peptides. As indicated earlier in the specification, the most striking example was PelB$^{SP}$, which was initially the worst performing signal peptide for production of β-lactamase, but the best performing following synthetic evolution of the TIR as illustrated in FIG. 2D. Thus, the performance of the signal peptide is largely coupled to the efficiency of translation initiation.

EXAMPLES

The following examples are not to be interpreted as limiting the scope of the invention. For experimental details pertaining to the examples below, the skilled reader is directed to the separate EXPERIMENTAL PROCEDURES section below.

Example 1—Production of Periplasmic Proteins with Commonly Used Signal Peptides Five signal peptides that are commonly used for the production of recombinant proteins in the periplasm of *E. coli* were selected (MalE$^{SP}$, OmpA$^{SP}$, PhoA$^{SP}$, DsbA$^{SP}$ and PelB$^{SP}$; see Table 1; see SEQ-ID 29-33). The coding sequences for these signal peptides were cloned into the commonly used pET28a expression plasmid, upstream of the coding sequence for β-lactamase (FIG. 1A). To determine how efficiently the signal peptides supported the synthesis and secretion of β-lactamase the expression plasmids were transformed into the *E. coli* strain BL21(DE3) pLysS and a mild induction protocol was used to initiate transcription (0.05 mM IPTG for 2 hours at 30° C.). Following the induction period, whole cells were collected, and proteins were separated by SDS-PAGE and immuno-blotted, so that the secreted (Mature) and non-secreted (Precursor) β-lactamase could be distinguished. The experiment indicated that there were large differences in production levels (FIG. 1B). MalE$^{SP}$, OmpA$^{SP}$, PhoA$^{SP}$, DsbA$^{SP}$ supported a comparatively high-level of β-lactamase production, whereas PelB$^{SP}$ did not. The experiment also indicated that there were significant differences in secretion efficiency between the different signal peptides. MalE$^{SP}$ and PelB$^{SP}$ were effective in supporting the secretion of β-lactamase to the periplasm, whereas OmpA$^{SP}$, PhoA$^{SP}$ and DsbA$^{SP}$ were deemed less effective as there was a prominent precursor band.

To evaluate the performance of the signal peptides with other recombinant proteins, they were fused to a single chain variable fragment that recognizes the human epidermal growth factor receptor protein 2 protein (scFv$^{HER2}$) and a soluble fragment of the periplasmic chaperone YfgM from *Francisella tularensis* (FtYfgM$^{45-170}$). Again, there were considerable differences in production levels across the different signal peptides (FIGS. 1C and D). Moreover, there were considerable differences between β-lactamase, scFv$^{HER2}$ and FtYfgM$^{45-170}$ (FIG. 1B vs C vs D). Taken together, these observations demonstrate that signal peptide performance is varied and unpredictable during the synthesis and secretion of recombinant periplasmic proteins. This conclusion is supported by a large body of published work, but a molecular explanation for the phenomenon remains elusive [3].

Example 2—Signal Peptide Performance is Coupled to Translation Initiation

The expression plasmids used in the previous experiments had been assembled by genetically sandwiching the nucleotide sequence encoding the signal peptide between the vector encoded 5'UTR and the 5' end of the mature coding sequence for β-lactamase, scFv$^{HER2}$ or FtYfgM45-170 (FIG. 2A). Each expression plasmid therefore contained a different TIR (Table 2). The inventors hypothesized that these TIRs might not be optimal for translation initiation as they had not co-evolved with the host cell ribosomes, possibly leading to unfavorable interactions at the mRNA level (FIG. 2B). They are therefore referred to as a TIR$^{UNEVOLVED}$.

Synthetic (or directed) evolution was used to select TIRs that were more compatible with the host cell ribosomes. In the experiment, TIR$^{LIBRARIES}$ were created from expression plasmids containing the MalE$^{SP}$, OmpA$^{SP}$, PhoA$^{SP}$, DsbA$^{SP}$ and PelB$^{SP}$ fused to β-lactamase. In the design of the TIR$^{LIBRARIES}$, the six nucleotides immediately upstream from the AUG start codon were completely randomized, and the six nucleotides immediately downstream from the AUG start codon were randomized with synonymous codon changes only (FIG. 2C) [34,35]. Each TIR$^{LIBRARY}$ theoretically contained >18,000 expression plasmids with a different TIR. The TIR$^{LIBRARIES}$ were transformed into BL21(DE3) pLysS and plated onto LB agar containing 0.05 mM IPTG and increasing concentrations of ampicillin (FIG. 2C). A colony that was resistant to a high concentration of ampicillin was selected, the expression plasmid was isolated and the TIR sequenced. These TIRs as referred to as synthetically evolved (TIR$^{SYN\_EVOLVED}$) (Table 2).

TABLE 2

Nucleotide sequences of the TIR$^{UNEVOLVED}$ and corresponding TIR$^{SYN\_EVOLVED}$ used in this study. The TIR is defined as the region from the Shine-Dalgarno to codon five of the signal peptide.

| Signal peptide | TIR | Sequence | Seq ID |
|---|---|---|---|
| MalE$^{SP}$ | UNEVOLVED | GTTTAACTTTAAGAAGGAGATATACCGATGAAAA TAAAAACAGGTGCACGC | 48/49 |
| | SYN_EVOLVED | GTTTAACTTTAAGAAGGAGATCGTATTATGAAAA TTAAAACAGGTGCACGC | 1/15 |
| | SYN_EVOLVED | GTTTAACTTTAAGAAGGAGATCATGGAATGAAG ATCAAAACAGGTGCACGC | 2/16 |
| | SYN_EVOLVED | GTTTAACTTTAAGAAGGAGATTAGTGGATGAAA ATAAAAACAGGTGCACGC | 3/17 |
| OmpA$^{SP}$ | UNEVOLVED | GTTTAACTTTAAGAAGGAGATATACCGATGAAAA AGACAGCTATCGCGATT | 50/51 |
| | SYN_EVOLVED | GTTTAACTTTAAGAAGGAGATGTTCGTATGAAGA AGACAGCTATCGCGATT | 4/18 |
| | SYN_EVOLVED | GTTTAACTTTAAGAAGGAGATAAGGAAATGAAG AAGACAGCTATCGCGATT | 5/19 |

TABLE 2-continued

Nucleotide sequences of the TIR$^{UNEVOLVED}$
and corresponding TIR$^{SYN\_EVOLVED}$ used in this
study. The TIR is defined as the region from the
Shine-Dalgarno to codon five of the signal peptide.

| Signal peptide | TIR | Sequence | Seq ID |
|---|---|---|---|
| | SYN_EVOLVED | GTTTAACTTTAAGAAGGAGATAATTCTATGAAAA AGACAGCTATCGCGATT | 6/20 |
| PhoA$^{SP}$ | UNEVOLVED | GTTTAACTTTAAGAAGGAGATATACCGATGAAAC AAAGCACTATTGCACTG | 52/53 |
| | SYN_EVOLVED | GTTTAACTTTAAGAAGGAGATTAACGTATGAAGC AAAGCACTATTGCACTG | 7/21 |
| | SYN_EVOLVED | GTTTAACTTTAAGAAGGAGATATTATGATGAAGC AAAGCACTATTGCACTG | 8/22 |
| DsbA$^{SP}$ | UNEVOLVED | GTTTAACTTTAAGAAGGAGATATACCGATGAAAA AGATTTGGCTGGCGCTG | 54/55 |
| | SYN_EVOLVED | GTTTAACTTTAAGAAGGAGATCGTAGGATGAAA AAGATTTGGCTGGCGCTG | 9/23 |
| | SYN_EVOLVED | GTTTAACTTTAAGAAGGAGATCGGTGGATGAAG AAAATTTGGCTGGCGCTG | 10/24 |
| | SYN_EVOLVED | GTTTAACTTTAAGAAGGAGATGGCTCCATGAAAA AGATTTGGCTGGCGCTG | 11/25 |
| PelB$^{SP}$ | UNEVOLVED | GTTTAACTTTAAGAAGGAGATATACCGATGAAAT ACCTGCTGCCGACCGCT | 56/57 |
| | SYN_EVOLVED | GTTTAACTTTAAGAAGGAGATATCAGGATGAAGT ATCTGCTGCCGACCGCT | 12/26 |
| | SYN_EVOLVED | GTTTAACTTTAAGAAGGAGATTCAAGTATGAAAT ATCTGCTGCCGACCGCT | 13/27 |
| | SYN_EVOLVED | GTTTAACTTTAAGAAGGAGATCTGTTTATGAAAT ATCTGCTGCCGACCGCT | 14/28 |

$^{1}$Underlined region was randomised during the synthetic evolution process
$^{2}$Nucleotides marked in bold text were changed in TIR$^{SYN\_EVOLVED}$
$^{3}$SEQ ID is indicated for underlined region (referred to as "short sequence" in the sequence listing) and full nucleotide sequence (referred to as "full sequence" in the sequence listing), respectively Expression plasmids containing either a TIR$^{UNEVOLVED}$ or TIR$^{SYN\_EVOLVED}$ were re-transformed into BL21(DE3) pLysS and the production levels of β-lactamase compared by immuno-blotting. After a two-hour induction period we observed that the production levels of periplasmic β-lactamase were significantly higher when using a TIR$^{SYN\_EVOLVED}$ compared to the TIR$^{UNEVOLVED}$ (FIG. 2D). Note that production of β-lactamase from each TIR$^{UNEVOLVED}$ was undetectable on these blots because the difference with the TIR$^{SYN\_EVOLVED}$ was too large to capture at this time point (see below). Consistent with this observation, disc diffusion assays confirmed that the TIR$^{SYN\_EVOLVED}$ supported a higher level of resistance to ampicillin than the TIR$^{UNEVOLVED}$ (FIG. 2E). FIGS. 2E and 2D illustrate comparative experiments using TIR$^{UNEVOLVED}$ and TIR$^{SYN\_EVOLVED}$ wherein (i) TIR$^{SYN\_EVOLVED}$ comprised SEQ ID 15, 18, 21, 23 and 26, and (ii) TIR$^{UNEVOLVED}$ comprised SEQ ID of 48, 50, 52, 54 and 56, respectively.

The inventors speculate that the difference in production levels from the TIR$^{UNEVOLVED}$/TIR$^{SYN\_EVOLVED}$ pairs was a result of mRNA relaxation, but the inventors were unable to support this speculation by using mRNA fold prediction programs. The lack of a correlation could reflect the fact that (1) mRNA relaxation is not the sole determinant, (2) mRNA structure is notoriously difficult to predict, and/or (2) existing algorithms only handle short stretches of nucleotides (not an entire mRNA). Nevertheless, the experiment does demonstrate that all signal peptides were under-performing when a TIR$^{UNEVOLVED}$ was used. And significantly, the performance of all signal peptides could be improved by synthetically evolving the TIR$^{UNEVOLVED}$. This phenomenon was most easily seen with PelB$^{SP}$, which gave the lowest levels of β-lactamase production when expressed from a TIR$^{UNEVOLVED}$ (FIG. 1B) but the highest when expressed from a TIR$^{SYN\_EVOLVED}$ (FIG. 2E). Synthetic evolution of the TIR had therefore 'converted' the PelB$^{SP}$ from a 'poor-performing' signal peptide to a 'top-performing' signal peptide without changing a single amino acid. The data therefore demonstrate that signal peptide performance is tightly coupled to translation initiation in bacterial cell factories.

Figure 3:
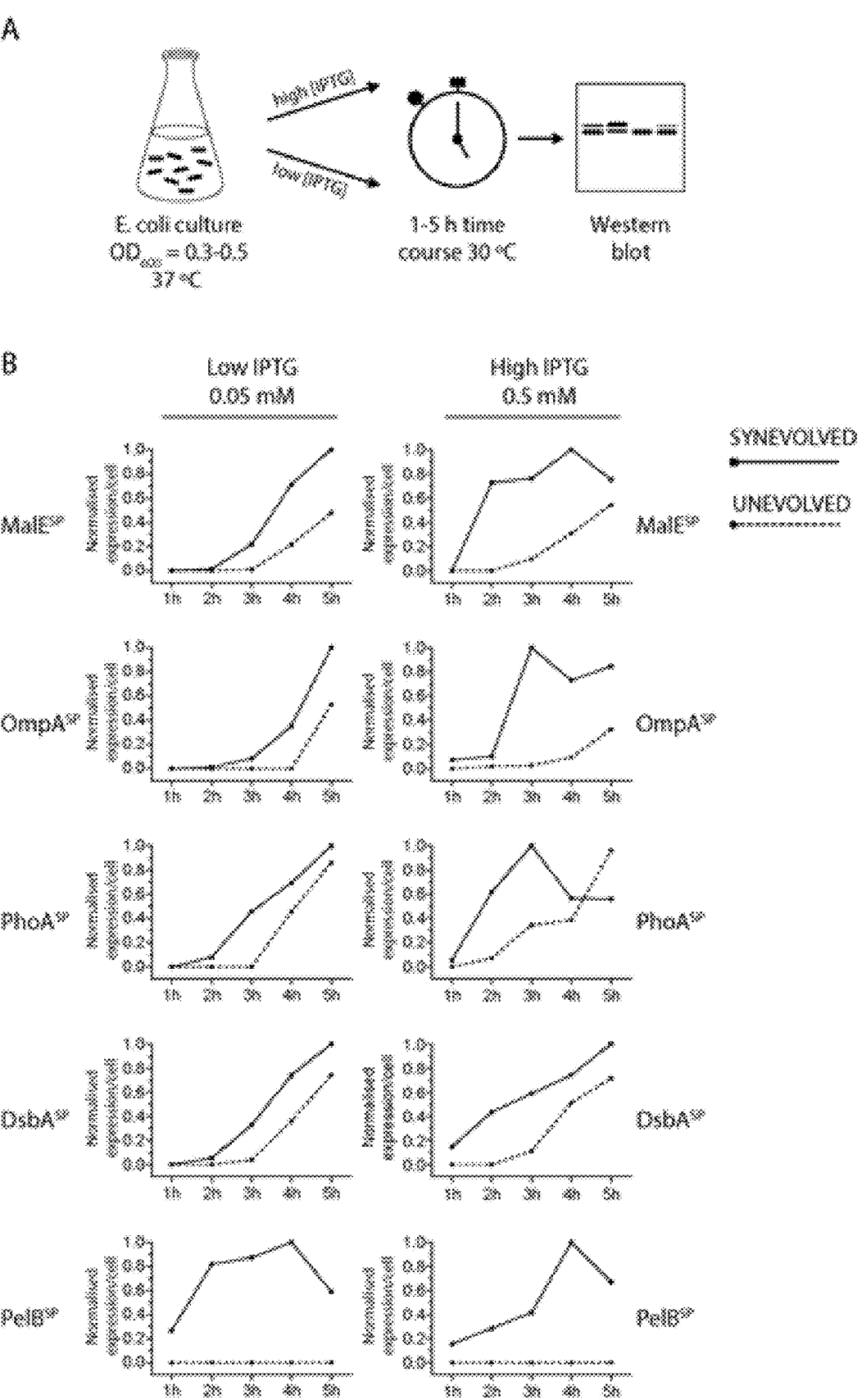
FIG. 3. Time-course analysis of β-lactamase production. (A) An illustration of the experimental workflow used. (B) At each time point, a volume of cells was extracted, then separated by SDS-PAGE and immuno-blotted with antisera to β-lactamase. Band intensities were obtained from immuno-blots by densitometric analysis and normalised to the highest-value.

Example 3—Production of Recombinant Periplasmic Proteins Using a TIR$^{SYN\_EVOLVED}$ In the previous series of experiments a mild induction protocol had been used (0.05 mM IPTG for 2 hours at 30° C.), so that differences in protein production could be assessed in the absence of a metabolic load on the cell. The concern about metabolic load largely relates to the Sec translocon, which is believed to be a bottleneck in the production of periplasmic proteins [36,37]. When production levels of periplasmic proteins are too high, the translocon could become saturated and the recombinant protein may be retained in the cytoplasm. To determine if expression plasmids with a TIR$^{SYN\_EVOLVED}$ would saturate the Sec translocon, the inventors induced with either a low (0.05 mM) or a high (0.5 mM) IPTG concentration and monitored production over a 5-hour period (FIG. 3A). It was observed that, at all but one time-point, a TIR$^{SYN\_EVOLVED}$ produced more periplasmic β-lactamase than the corresponding TIR$^{UNEVOLVED}$ (FIG. 3B). This observation was made at both low and high concentrations of IPTG. These time-course experiments therefore indicated that the Sec translocon was able to cope with the increased production levels that were reached using a $TIR^{SYN\_EVOLVED}$. FIG. 3B illustrates comparative experiment using $TIR^{UNEVOLVED}$ and $TIR^{SYN\_EVOLVED}$ wherein (i) $TIR^{SYN\_EVOLVED}$ comprised SEQ ID 15, 18, 21, 23 and 26, and (ii) $TIR^{UNEVOLVED}$ comprised SEQ ID of 48, 50, 52, 54 and 56, respectively.

Example 4—Using $TIR^{SYN\_EVOLVED}$ as a Generic Solution

Figure 4:
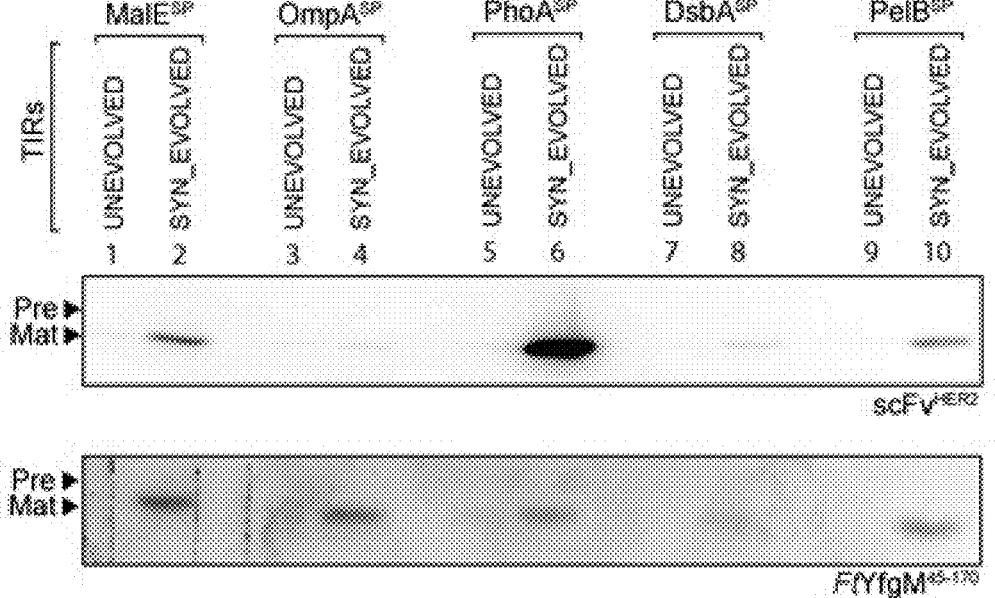
FIG. 4. A synthetically evolved TIR (TIR$^{SYN\_EVOLVED}$) is transferable. (A) Expression levels of ScFv$^{HER2}$ and FtYfgM$^{45-170}$ using five different signal peptides. In each instance TIR$^{UNEVOLVED}$/TIR$^{SYN\_EVOLVED}$ pairs were assessed by immuno-blotting. The TIR$^{SYN\_EVOLVED}$ had originally been selected for β-lactamase (see FIG. 2). In this experiment, protein production was induced for two hours, then a volume of cells corresponding to 0.2 OD$_{600}$ units of cells were harvested, separated by a 12% SDS-PAGE and protein levels were determined by immunoblotting with antisera to a poly-histidine tag. 'Pre' denotes the precursor form of the protein and 'Mat' denotes the mature version.

In this set of experiments the coding sequences of scFvHER2 and $FtYfgM^{45-170}$ were expressed as fusions to the original five signal peptides, using both the $TIR^{UNEVOLVED}$ and $TIR^{SYN\_EVOLVED}$ pairs. The expression plasmids were again transformed into BL21(DE3) pLysS and production was monitored using a mild induction protocol (0.05 mM IPTG for 2 hours at 30° C.). As we had observed for β-lactamase, the $TIR^{SYN\_EVOLVED}$ always produced more protein than the corresponding $TIR^{UNEVOLVED}$ (FIG. 4). It was noted that signal peptide performance was varied; the most effective signal peptide for production of $scFv^{HER2}$ was $PhoA^{SP}$, whilst the most effective for $FtYfgM^{45-170}$ was $MalE^{SP}$. Thus, signal peptide performance might partly be explained by compatibility with the signal peptide. FIG. 4 illustrates comparative experiments using $TIR^{UNEVOLVED}$ and $TIR^{SYN\_EVOLVED}$ wherein (i) $TIR^{SYN\_EVOLVED}$ comprised SEQ ID 15, 18, 21, 23 and 26, and (ii) $TIR^{UNEVOLVED}$ comprised SEQ ID of 48, 50, 52, 54 and 56, respectively.

Figure 5:
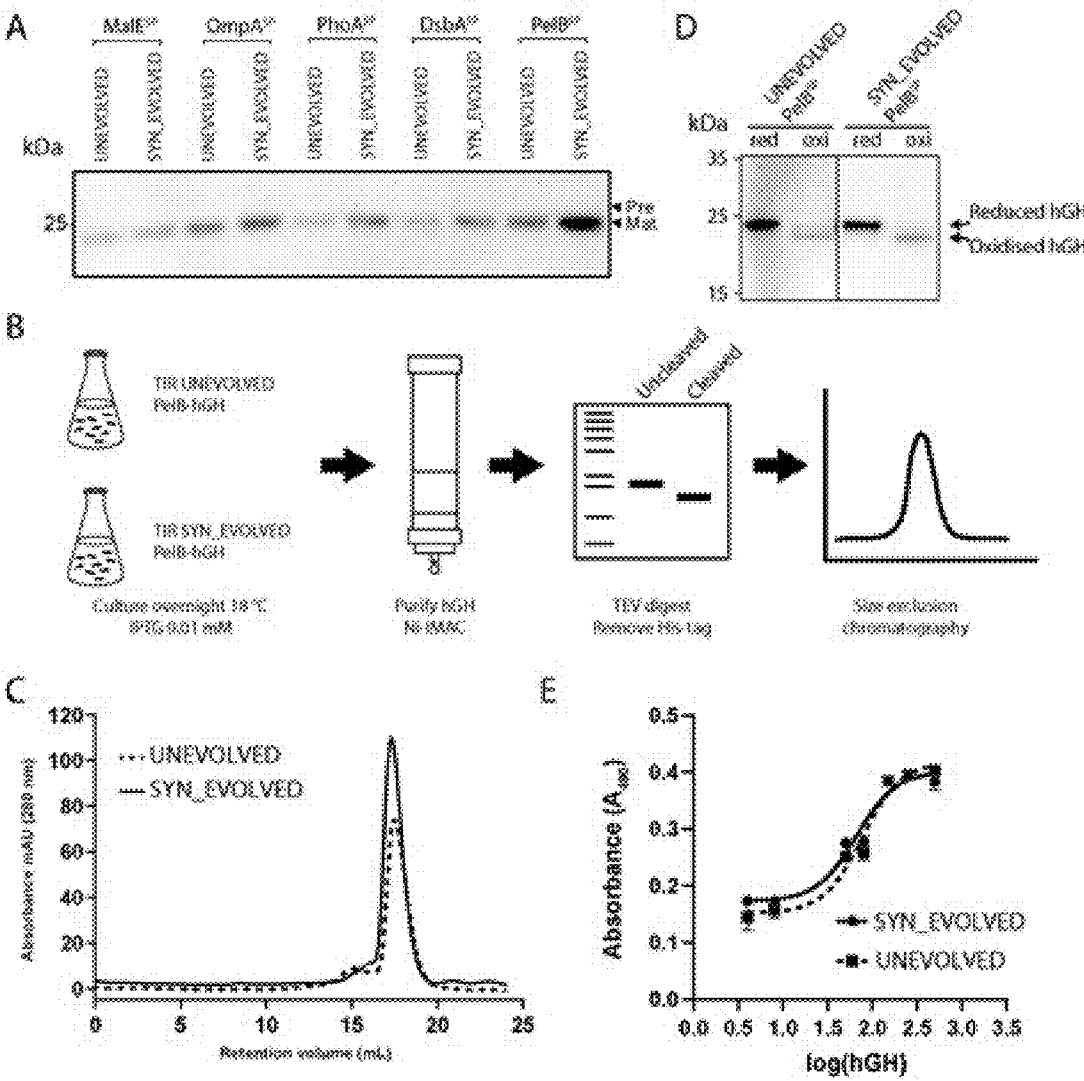
FIG. 5. Production and purification of the human growth hormone (hGH) using a TIR$^{SYN\_EVOLVED}$. (A) Production levels of hGH using five different signal peptides. In each instance the difference between TIR$^{UNEVOLVED}$/TIR$^{SYN\_EVOLVED}$ pairs were assessed by immuno-blotting. The TIR$^{SYN\_EVOLVED}$ had originally been selected for β-lactamase (see FIG. 2). In this experiment, protein production was induced for two hours, then a volume of cells corresponding to 0.2 OD$_{600}$ units of cells were harvested, separated by a 12% SDS-PAGE and protein levels were determined by immuno-blotting with antisera to a poly-histidine tag. 'Pre' denotes the precursor form of the protein and 'Mat' denotes the mature version. (B) An overview of the methodology used to purify hGH. (C) Analysis of the purified hGH by Size-Exclusion Chromatography (SEC). (D) Purified hGH was analysed by SDS-PAGE under denaturing- and non-denaturing conditions. (E) Activity of the purified hGH by using the MTS cell proliferation assay.

A similar approach was taken to produce the human growth hormone (hGH). Here we observed that the most effective $TIR^{SYN\_EVOLVED}$ for production of hGH was the one coupled to the $PelB^{SP}$ (FIG. 5A). To assess how much more protein was produced the N-terminally His-tagged hGH was purified by Immobilized Metal Affinity Chromatography (IMAC), the His-tag removed by proteolytic processing, and the sample polished by Size Exclusion Chromatography (SEC) (FIG. 5B). The yield of purified hGH was more than 3-fold higher using the $TIR^{SYN\_EVOLVED}$ compared to the $TIR^{UNEVOLVED}$ (2.56 mg/L vs 0.79 mg/L). Importantly, we could not detect any difference in the quality of the purified hGH, as judged by monodispersity of the sample following SEC (FIG. 5C), the proportion of protein that had formed disulphide bonds (FIG. 5D), or the activity of the protein when tested by the MTS cell proliferation assay (FIG. 5E). FIGS. 5A, 5C, 5D and 5E illustrate comparative experiments using $TIR^{UNEVOLVED}$ and $TIR^{SYN\_EVOLVED}$ wherein (i) $TIR^{SYN\_EVOLVED}$ comprised SEQ ID 15, 18, 21, 23 and 26, and (ii) $TIR^{UNEVOLVED}$ comprised SEQ ID of 48, 50, 52, 54 and 56, respectively.

Taken together, this series of experiments indicate that the pET28a-based vectors containing signal peptides with a $TIR^{SYN\_EVOLVED}$ can be used as a generic solution to increase production of single chain antibody fragments, hormones and other recombinant proteins in the periplasm of E. coli without compromising protein quality.

EXPERIMENTAL PROCEDURES

Molecular Cloning

The sequences encoding $MalE^{SP}$, $OmpA^{SP}$, $PhoA^{SP}$, $DsbA^{SP}$, $PelB^{SP}$, β-lactamase, hGH and $FtYfgM^{45-170}$ were chemically synthesised (Genscript, USA). The sequence encoding $scFv^{HER2}$ was obtained from the pHP2-15 plasmid [44]. To generate expression clones, the coding sequences and the pET28a vector were amplified by PCR using the Q5 polymerase (New England Biolabs, UK). The coding sequences were then cloned between the NcoI and NdeI restriction enzyme sites using the Gibson cloning method. Enzymes used for Gibson cloning were obtained from New England Biolabs, UK.

Synthetic Evolution of the TIR $TIR^{LIBRARIES}$ were generated by amplifying the expression plasmids by PCR, using overlapping primers as previously described [34,35]. The forward primer was approximately 45 nucleotides in length and was partly degenerate. The design enabled complete randomization of the six nucleotides upstream of the AUG start codon, and partial randomization of the six nucleotides downstream stream of the AUG start codon (synonymous codons only). The reverse primer was always the same sequence (5'-CTCCTTCTTAAAGTTAAACAAAATTAT-TTCTAGAGGGGAATTGTTATC-3'). It overlapped with the forward primer by 13 nucleotides thus allowing circularization of the PCR product by homologous recombination in E. coli MC1061. The PCR was carried out using the Q5 polymerase (New England Biolabs, UK) in a program that consisted of 94° C. for 5 min and then 30 cycles of 95° C. for 45 s, 48-68° C. for 45 s (using a gradient thermocycler), 72° C. for 6 min and a final elongation step of 72° C. for 5 min. Specific PCR products that were amplified at the lowest annealing temperature were treated with DpnI, then transformed into chemically competent E. coli MC1061. The transformation was seeded into 100 mL of Luria-Bertani containing 50 µg/mL kanamycin and incubated overnight at 37° C. Isolation of the $TIR^{LIBRARIES}$ was carried out using ten E.N.Z.A DNA mini kit purification columns (Omega Biotek, USA) and pooling of the eluates.

$TIR^{LIBRARIES}$ were screened by transforming chemically competent BL21(DE3) pLysS and identifying clones that survived on the highest concentration of ampicillin. Here 0.5 µg of the $TIR^{LIBRARY}$ was transformed into 50 µL of chemically competent BL21(DE3) pLysS using standard protocols. The entire transformation was then seeded into 3 mL of LB containing 50 µg/mL kanamycin and 34 µg/mL chloramphenicol. Cultures were grown at 37° C. with shaking for 16 h. Cultures were then back-diluted (1:50) into 5 mL of LB containing 50 µg/mL kanamycin and 34 µg/mL chloramphenicol and incubated as before until an $OD_{600}$ of ~0.3 was reached. Expression of the coding sequence was induced by streaking a volume of cells corresponding to 0.002 $OD_{600}$ units on LB agar containing 0.05 mM isopropyl-β-D thio-galactopyranoside (IPTG) and increasing concentrations of ampicillin (100-5000 µg/mL).

Note that kanamycin and chloramphenicol were omitted from the plates. The plates were then incubated for 16 h at 37° C. Colonies formed at higher ampicillin concentrations were selected for further analysis and sequencing (Eurofins MWG operon, Germany).

Immuno-Blotting

Cultures were grown at 37° C. with shaking for 16 h, then back-diluted (1:50) into 5 mL of LB containing 50 µg/mL kanamycin and 34 µg/mL chloramphenicol and incubated as before until an $OD_{600}$ of ~0.3-0.5 was reached. Expression of the coding sequence was induced with 0.05 mM IPTG for 2 h at 30° C. A volume of cells corresponding to an $OD_{600}$ of either 0.02 or 0.2 was harvested by centrifugation then resuspended in 2× Laemlli loading buffer [125 mM Tris-HCl pH 6.8, 4% SDS, 3% Glycerol, 0.02% bromophenol blue, 20% β-mercaptoethanol]. Proteins were separated by 12% SDS-PAGE then transferred to a nitrocellulose membrane using a semi-dry transfer apparatus (Bio-Rad, USA). The nitrocellulose membranes were probed with an antibody against either β-lactamase (Thermo Scientific, USA) or the poly-histidine tag (His-Probe, ThermoFisher Scientific, USA). Binding was detected using anti-mouse IgG linked to horseradish peroxidase (GE healthcare, USA) and a Super-Signal West femto luminol/enhancer solution (ThermoFisher Scientific, USA). Luminescence emitting from the nitrocellulose membrane was detected using an Azure Biosystems c600 device.

Disc Diffusion Assays

Cells were grown in LB containing 50 µg/mL kanamycin and 34 µg/mL chloramphenicol until an $OD_{600}$ of ~0.3. A volume of cells corresponding to an $OD_{600}$ of 0.002 was then plated onto LB agar (lacking all antibiotics). A sterile filter disc containing 2 mg ampicillin was then placed on top of the cells and the plates were incubated at 37° C. for 16 h. Zones of growth inhibition were measured using a standard ruler.

Purification of hGH

Expression plasmids harboring pET28a pelB-hGH were transformed into the expression host BL21(DE3) pLysS and grown on LB agar plates containing 50 µg/mL kanamycin and 34 µg/mL chloramphenicol. Single colonies were used to inoculate 100 mL of LB plus antibiotics medium which was grown overnight at 37° C. with shaking at 180 RPM. Overnight pre-cultures were used to inoculate 2 L flasks containing 1 L of LB media plus antibiotics, to a starting $OD_{600}$ of 0.05. Cultures were grown to an $OD_{600}$ of 0.7, at which point, flasks were incubated on ice for 10 minutes. Induction proceeded with the addition of 0.01 mM IPTG and incubation for 16 hours at 18° C. with shaking at 180 RPM. Cells were harvested for 20 minutes at 4,000×g. Cell pellets were resuspended in 50 mL suspension buffer (50 mM Tris pH 8.0, 500 mM NaCl, 20 mM imidazole pH 8.0 and 1× protease inhibitor cocktail (complete, Roche, USA)). Cell suspensions were homogenized with a glass Dounce homogenizer followed by cell disruption using an Avestin emulsiflex C3 high-pressure homogenizer (Avestin, Canada). Cell debris was removed by centrifugation at 20,000×g for 30 minutes. Samples were applied to 2.5 mL Ni-sepharose (GE Healthcare) and batch incubated at 4° C. for one hour on a benchtop roller. The column was washed with 20 column volumes (50 mL) of wash buffer (50 mM Tris pH 8.0, 500 mM NaCl and 50 mM imidazole pH 8.0), followed by elution with 30 mL of elution buffer (50 mM Tris pH 8.0, 500 mM NaCl and 500 mM imidazole pH 8.0). The elution fraction was concentrated and buffer exchanged (50 mM Tris pH 8.0, 150 mM NaCl and 20 mM imidazole) using a centrifugal filter with a nominal MWCO of 10 kDa (Amicon, Merck Millipore). The N-terminal his-tag was proteolytically removed with TEV protease (purified in-house) at a 1:10 weight ratio and allowed to incubate overnight at 4° C. Samples were reverse Ni purified, concentrated and applied to size exclusion chromatography using a Superdex 200 10/300 GL column (GE Healthcare, Sweden) in 50 mM Tris pH 8.0 and 100 mM NaCl. Relevant fractions were pooled, and concentrated. Sample concentration was measured by the BCA protein assay kit (Pierce, ThermoFisher Scientific, USA) and protein quality assessed by SDS-PAGE. Calculation of final yield per liter was determined by accounting of final volume, final OD at the conclusion of expression, and final concentration of purified hGH.

MTS Cell Proliferation Assay

The breast cancer MCF7 cell line (ATCC) was maintained in RPMI-1640 medium containing 10% FBS, 2 mM glutamine and 1% penicillin streptomycin (Gibco/Thermo Fisher Scientific) at 37° C. in a humidified atmosphere at 5% $CO_2$.

Cell proliferation following titration of purified hGH was determined according to the CellTiter 96 AQueous Non-Radioactive Cell Proliferation assay (MTS) protocol (Promega). Briefly, $1×10^4$ MCF7 cells were seeded in triplicate, in 100 µL aliquots into 96 well plates, followed by serum starvation for 24 hours, prior to commencing the proliferation assay. Serially diluted hGH was added to the medium at a final concentration ranging from 0 to 400 ng/mL. Cell proliferation was assessed after 48 hours of incubation, by addition of MTS and the electron coupling reagent PMS. The conversion of MTS to formazan was measured by absorbance at 490 nm using a SpectraMax plate reader. Background absorbance was corrected by subtraction of wells containing RPMI. hGH EC50 was calculated using GraphPad Prism 8.1.0.

REFERENCES

1. Walsh, G. Biopharmaceutical benchmarks 2014. Nat. Biotechnol. 32, 992-1000 (2014).
2. Singh, R., Kumar, M., Mittal, A. & Mehta, P. K. Microbial enzymes: industrial progress in 21st century. 3 Biotech 6, 174 (2016).
3. Freudl, R. Signal peptides for recombinant protein secretion in bacterial expression systems. Microb. Cell Factories 17, 52 (2018).
4. Berkmen, M. Production of disulfide-bonded proteins in *Escherichia coli*. Protein Expr. Purif. 82, 240-251 (2012).
5. Manta, B., Boyd, D. & Berkmen, M. Disulfide Bond Formation in the Periplasm of *Escherichia coli*. EcoSal Plus 8, (2019).
6. Crane, J. M. & Randall, L. L. The Sec System: Protein Export in *Escherichia coli*. EcoSal Plus 7, (2017).
7. Tsirigotaki, A., De Geyter, J., Šoštaric', N., Economou, A. & Karamanou, S. Protein export through the bacterial Sec pathway. Nat. Rev. Microbiol. 15, 21-36 (2017).
8. von Heijne, G. Signal sequences. The limits of variation. J. Mol. Biol. 184, 99-105 (1985).
9. von Heijne, G. The signal peptide. J. Membr. Biol. 115, 195-201 (1990).
10. Power, P. M., Jones, R. A., Beacham, I. R., Bucholtz, C. & Jennings, M. P. Whole genome analysis reveals a high incidence of non-optimal codons in secretory signal sequences of *Escherichia coli*. Biochem. Biophys. Res. Commun. 322, 1038-1044 (2004).
11. Biased codon usage in signal peptides: a role in protein export. Trends Microbiol. 17, 146-150 (2009).
12. Zalucki, Y. M., Power, P. M. & Jennings, M. P. Selection for efficient translation initiation biases codon usage at second amino acid position in secretory proteins. Nucleic Acids Res. 35, 5748-5754 (2007).
13. Zalucki, Y. M., Gittins, K. L. & Jennings, M. P. Secretory signal sequence non-optimal codons are required for expression and export of beta-lactamase. Biochem. Biophys. Res. Commun. 366, 135-141 (2008).
14. Zalucki, Y. M., Beacham, I. R. & Jennings, M. P. Coupling between codon usage, translation and protein export in *Escherichia coli*. Biotechnol. J. 6, 660-667 (2011).
15. Park, S., Liu, G., Topping, T. B., Cover, W. H. & Randall, L. L. Modulation of folding pathways of exported proteins by the leader sequence. Science 239, 1033-1035 (1988).

16. Gouridis, G., Karamanou, S., Gelis, I., Kalodimos, C. G. & Economou, A. Signal peptides are allosteric activators of the protein translocase. Nature 462, 363-367 (2009).

17. Laursen, B. S., Sørensen, H. P., Mortensen, K. K. & Sperling-Petersen, H. U. Initiation of Protein Synthesis in Bacteria. Microbiol. Mol. Biol. Rev. 69, 101-123 (2005).

18. McCarthy, J. E. & Gualerzi, C. Translational control of prokaryotic gene expression. Trends Genet. TIG 6, 78-85 (1990).

19. Ingolia, N. T., Ghaemmaghami, S., Newman, J. R. S. & Weissman, J. S. Genome-wide analysis in vivo of translation with nucleotide resolution using ribosome profiling. Science 324, 218-223 (2009).

20. Kozak, M. Regulation of translation via mRNA structure in prokaryotes and eukaryotes. Gene 361, 13-37 (2005).

21. Milón, P. & Rodnina, M. V. Kinetic control of translation initiation in bacteria. Crit. Rev. Biochem. Mol. Biol. 47, 334-348 (2012).

22. Schmeing, T. M. & Ramakrishnan, V. What recent ribosome structures have revealed about the mechanism of translation. Nature 461, 1234-1242 (2009).

23. Reeve, B., Hargest, T., Gilbert, C. & Ellis, T. Predicting translation initiation rates for designing synthetic biology. Front. Bioeng. Biotechnol. 2, 1 (2014).

24. Shine, J. & Dalgarno, L. Determinant of cistron specificity in bacterial ribosomes. Nature 254, 34-38 (1975).

25. Villegas, A. & Kropinski, A. M. An analysis of initiation codon utilization in the Domain Bacteria-concerns about the quality of bacterial genome annotation. Microbiology 154, 2559-2661 (2008).

26. Osterman, I. A., Evfratov, S. A., Sergiev, P. V. & Dontsova, O. A. Comparison of mRNA features affecting translation initiation and reinitiation. Nucleic Acids Res. 41, 474-486 (2013).

27. Espah Borujeni, A. et al. Precise quantification of translation inhibition by mRNA structures that overlap with the ribosomal footprint in N-terminal coding sequences. Nucleic Acids Res. 45, 5437-5448 (2017).

28. Goodman, D. B., Church, G. M. & Kosuri, S. Causes and effects of N-terminal codon bias in bacterial genes. Science 342, 475-479 (2013).

29. Bentele, K., Saffert, P., Rauscher, R., Ignatova, Z. & Blüthgen, N. Efficient translation initiation dictates codon usage at gene start. Mol. Syst. Biol. 9, 675 (2013).

30. Mortimer, S. A., Kidwell, M. A. & Doudna, J. A. Insights into RNA structure and function from genome-wide studies. Nat. Rev. Genet. 15, 469-479 (2014).

31. Scharff, L. B., Childs, L., Walther, D. & Bock, R. Local absence of secondary structure permits translation of mRNAs that lack ribosome-binding sites. PLOS Genet. 7, e1002155 (2011).

32. Kudla, G., Murray, A. W., Tollervey, D. & Plotkin, J. B. Coding-sequence determinants of gene expression in Escherichia coli. Science 324, 255-258 (2009).

33. Plotkin, J. B. & Kudla, G. Synonymous but not the same: the causes and consequences of codon bias. Nat. Rev. Genet. 12, 32-42 (2011).

34. Mirzadeh, K. et al. Enhanced Protein Production in Escherichia coli by Optimization of Cloning Scars at the Vector-Coding Sequence Junction. ACS Synth. Biol. 4, 959-965 (2015).

35. DALEY, D., MIRZADEH, K., TODDO, S., GUNTUR, S. & Ab, C. Selective optimisation of a ribosome binding site for protein production. (2015).

36. Hjelm, A. et al. Tailoring Escherichia coli for the l-Rhamnose PBAD Promoter-Based Production of Membrane and Secretory Proteins. ACS Synth. Biol. 6, 985-994 (2017).

37. Schlegel, S. et al. Optimizing heterologous protein production in the periplasm of E. coli by regulating gene expression levels. Microb. Cell Factories 12, 24 (2013).

38. Punginelli, C. et al. mRNA Secondary Structure Modulates Translation of Tat-Dependent Formate Dehydrogenase N. J. Bacteriol. 186, 6311-6315 (2004).

39. Ng, D. T. W. & Sarkar, C. A. Engineering Signal Peptides for Enhanced Protein Secretion from Lactococcus lactis. Appl. Environ. Microbiol. 79, 347-356 (2013).

40. Karyolaimos, A. et al. Enhancing recombinant protein yields in the E. coli periplasm by combining signal peptide and production rate screening. Front. Microbiol. 10, (2019).

41. Rennig, M. et al. TARSyn: Tunable Antibiotic Resistance Devices Enabling Bacterial Synthetic Evolution and Protein Production. ACS Synth. Biol. 7, 432-442 (2018).

42. Rennig, M., Daley, D. O. & Nørholm, M. H. H. Selection of Highly Expressed Gene Variants in Escherichia coli Using Translationally Coupled Antibiotic Selection Markers. Methods Mol. Biol. Clifton NJ 1671, 259-268 (2018).

43. Ferro, R., Rennig, M., Hernández-Rollán, C., Daley, D. O. & Nørholm, M. H. H. A synbio approach for selection of highly expressed gene variants in Gram-positive bacteria. Microb. Cell Factories 17, 37 (2018).

44. Hu, F. J. et al. Combination of phage and Gram-positive bacterial display of human antibody repertoires enables isolation of functional high affinity binders. New Biotechnol. 45, 80-88 (2018).

The invention claimed is:

1. A DNA construct suitable for regulating signal peptide performance, wherein said DNA construct comprises:

a. a Shine-Dalgarno sequence;

b. an ATG start codon;

c. a sequence of one of SEQ ID 1-28 comprising said ATG start codon; and d. a signal peptide encoding sequence, wherein said sequence of one of SEQ ID 1-28 comprises at least the first 9 nucleotides of said signal peptide encoding sequence;

wherein said sequence of one of SEQ ID NO 15-28 comprises said Shine-Dalgarno sequence, said ATG start codon and said sequence of one of SEQ ID 1-14.

2. The DNA construct according to claim 1, wherein said signal peptide encoding sequence comprises a sequence for expressing a signal peptide selected from MalE, OmpA, PhoA, DsbA, and Pelb.

3. The DNA construct according to claim 1, wherein said signal peptide encoding sequence is a sequence of one of SEQ ID 34-47.

4. The DNA construct according to claim 1, wherein said signal peptide encoding sequence expresses a signal peptide of a sequence of one of SEQ ID 29-33.

5. The DNA construct according to claim 1, wherein said Shine-Dalgarno sequence comprises nucleotide sequence TAAGAAGG in the direction of transcription.

6. The DNA construct according to claim 3, wherein:

said MalE signal peptide encoding sequence of one of SEQ ID 34, 35 and 36 expresses a signal peptide of a sequence of one of SEQ ID 29;

said OmpA signal peptide encoding sequence of one of SEQ ID 37, 38 and 39 expresses a signal peptide of a sequence of one of SEQ ID 30;

said PhoA signal peptide encoding sequence of one of SEQ ID 40 and 41 expresses a signal peptide of a sequence of one of SEQ ID 31;

said DsbA signal peptide encoding sequence of one of SEQ ID 42, 43 and 44 expresses a signal peptide of a sequence of one of SEQ ID 32; and/or said PelB signal peptide encoding sequence of one of SEQ ID 45, 46 and 47 expresses a signal peptide of a sequence of one of SEQ ID 33.

7. The DNA construct according to claim 1, wherein said DNA construct comprise a sequence of one of SEQ ID 15, 18, 21, 23 and 26.

8. The DNA construct according to claim 1, wherein said DNA construct further comprises a recombinant protein encoding sequence.

9. The DNA construct according to claim 8, wherein said signal peptide encoding sequence is operably linked to said recombinant protein encoding sequence in the direction of transcription.

10. An expression vector comprising the DNA construct according to claim 1, wherein the expression vector is preferably a plasmid, more preferably PET expression vector, and most preferably pet28A.

11. A host cell comprising the vector according to claim 10, wherein said host cell is preferably a bacterial cell, more preferably said bacterial cell is *E. coli* and most preferably *E. coli* strain BL2l(DE3) pLysS.

12. RNA expressed by a DNA construct according to claim 1.

13. A method of using a DNA construct according to claim 1, for regulating signal peptide performance, comprising the steps of:

a. introducing the DNA construct according to claim 1 into an expression vector;

b. introducing the expression vector into a host cell; and c. growing the host cell.

14. A method of expressing a recombinant protein, comprising the steps of:

a. introducing a DNA construct according to claim 8 into an expression vector;

b. introducing the expression vector into a host cell;

c. growing the host cell; and d. recovering the recombinant protein from the host cell.

* * * * *